United States Patent
Regits et al.

(10) Patent No.: US 8,524,167 B2
(45) Date of Patent: Sep. 3, 2013

(54) CHLORINE DIOXIDE DECONTAMINATION SYSTEM AND METHOD

(76) Inventors: Michael A. Regits, Bethlehem, PA (US); Henry S. Luftman, Emmaus, PA (US); Paul W. Lorcheim, Lebanon, NJ (US)

( * ) Notice: Subject to any disclaimer, the term of this patent is extended or adjusted under 35 U.S.C. 154(b) by 415 days.

(21) Appl. No.: 12/759,929

(22) Filed: Apr. 14, 2010

(65) Prior Publication Data
US 2010/0266448 A1  Oct. 21, 2010

Related U.S. Application Data

(60) Provisional application No. 61/168,953, filed on Apr. 14, 2009.

(51) Int. Cl.
*A61L 2/00* (2006.01)
*A61L 9/00* (2006.01)
*A61L 2/18* (2006.01)

(52) U.S. Cl.
USPC ............... 422/300; 422/292; 422/28; 422/29; 422/30; 422/31

(58) Field of Classification Search
USPC .......................... 422/292, 300, 28, 29, 30, 31
See application file for complete search history.

(56) References Cited

U.S. PATENT DOCUMENTS

| | | |
|---|---|---|
| 4,104,190 A | 8/1978 | Hartshorn |
| 4,504,442 A | 3/1985 | Rosensblatt et al. |
| 4,681,739 A | 7/1987 | Rosenblatt et al. |
| 5,234,678 A | 8/1993 | Rosenblatt et al. |
| 5,320,817 A | 6/1994 | Hardwick et al. |
| 5,611,920 A | 3/1997 | Simpson et al. |
| 6,171,558 B1 | 1/2001 | Simpson |
| 6,235,240 B1 | 5/2001 | Heredia et al. |
| 7,335,243 B2 | 2/2008 | Homan et al. |
| 2003/0080317 A1 | 5/2003 | Speronello et al. |
| 2003/0086820 A1 | 5/2003 | McDonnell et al. |
| 2003/0133834 A1* | 7/2003 | Karle ............................. 422/33 |
| 2004/0047776 A1 | 3/2004 | Thomsen |
| 2005/0220666 A1 | 10/2005 | Foster |
| 2006/0107635 A1 | 5/2006 | Homan et al. |

OTHER PUBLICATIONS

International Search Report and Written Opinion issued Jul. 10, 2010 in counterpart application No. PCT/US10/31011.

* cited by examiner

*Primary Examiner* — Regina M Yoo
(74) *Attorney, Agent, or Firm* — Duane Morris LLP

(57) ABSTRACT

A system includes a portable source of gaseous chlorine dioxide (CD). The source has first source and return couplings for sealingly connecting to a CD generation flow path comprising at least one gas conduit. The CD generation flow path comprises second source and return couplings for sealingly connecting the source to a device to be treated with the CD generation flow path, or a tent structure enclosing the device to be treated. A portable scrubber has third couplings for sealingly connecting to a scrubbing flow path comprising at least one gas conduit for removing the CD from the device or tent structure. The gas conduit has fourth couplings for connecting the device or tent structure to the scrubbing flow path.

27 Claims, 18 Drawing Sheets

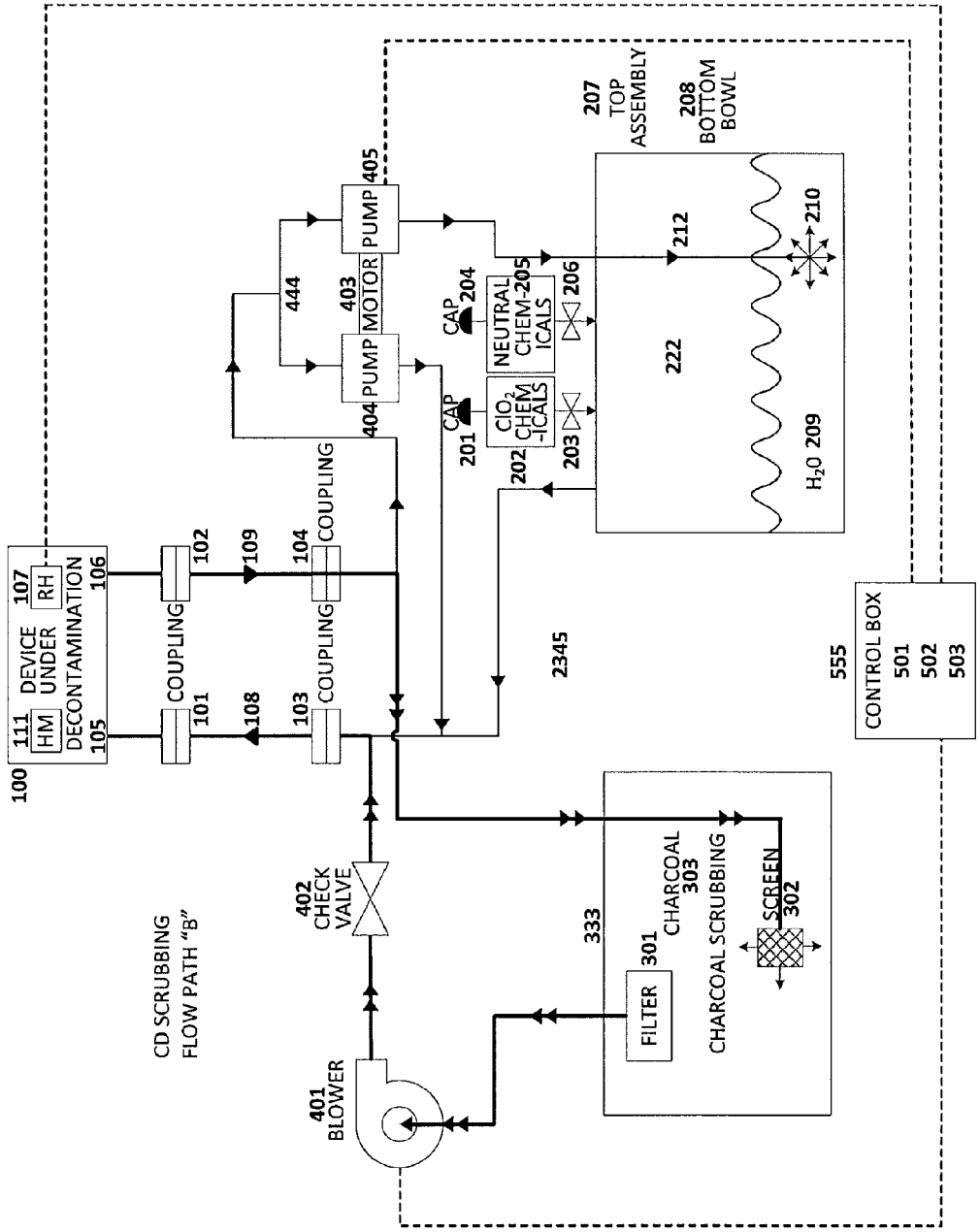

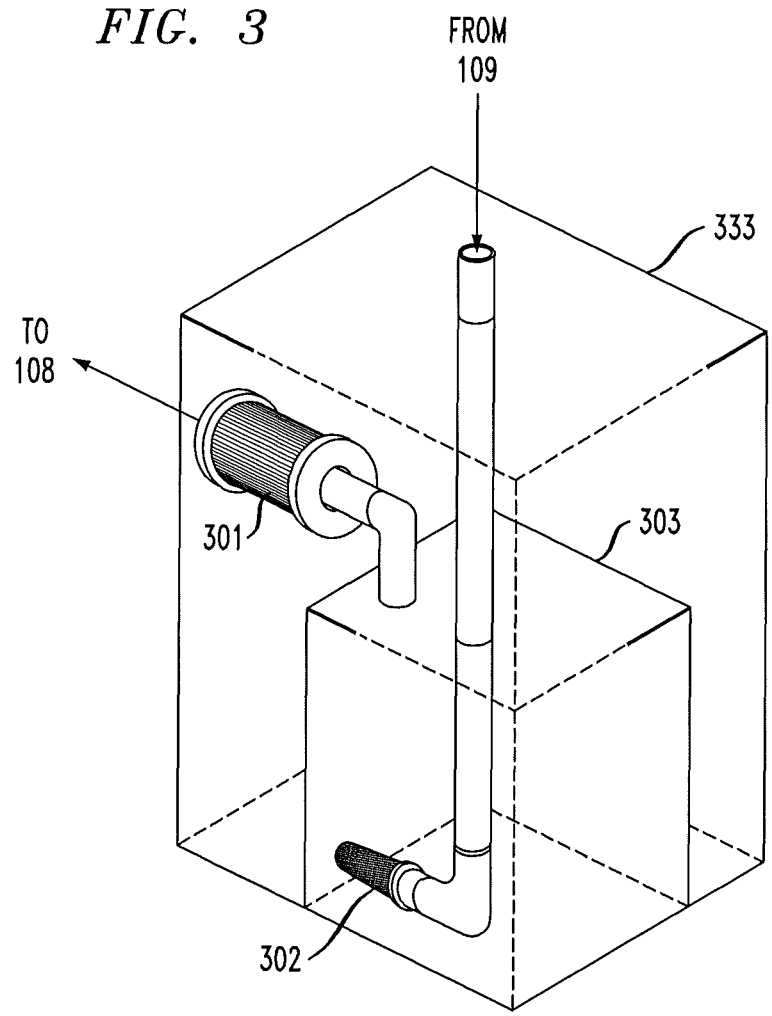

CHLORINE DIOXIDE DECONTAMINATION SYSTEM AND METHOD

This application claims the benefit of U.S. Provisional Patent Application No. 61/168,953, filed Apr. 14, 2009, which is incorporated by reference herein in its entirety.

FIELD OF THE INVENTION

The present invention relates to decontamination systems and methods.

BACKGROUND

Class I or Class II (laminar flow) biological safety cabinets are designed to minimize hazards inherent in work with biological agents. BSC's can be used for work with biological agents assigned to biosafety levels 1 through 4, depending on the facility design as described in the CDC/NIH publication Biosafety in Microbiological and Biomedical Laboratories. A BSC is a ventilated device for personnel, product, and environmental protection having an open front with inward airflow for personnel protection, downward HEPA filtered laminar airflow for product protection, and HEPA filtered exhausted air for environmental protection.

Recommendations and requirements to certify BSC's come from a variety of sources. All manufacturers and NSF International recommend field certification of BSC's. The Center for Disease Control (CDC) and NIH state that it is essential that Class I, II and III BSC's be tested and certified.

Decontamination is a key component of certification.

SUMMARY

In some embodiments, a system comprises a portable source of gaseous chlorine dioxide (CD). The source has couplings for sealingly connecting to a CD generation flow path comprising at least one gas conduit. A source panel and a return panel are provided, each having at least one fitting sealingly coupled thereto, for connecting to the at least one gas conduit. A flexible tent is sealingly coupled to the source panel and return panel so as to form a sealed enclosure for containing a device to be treated with the CD.

In some embodiments, a system comprises a portable source of gaseous chlorine dioxide (CD). The source has first source and return couplings for sealingly connecting to a CD generation flow path comprising at least one gas conduit. The CD generation flow path comprises second source and return couplings for sealingly connecting the source to a device to be treated with the CD generation flow path. A portable scrubber has third couplings for sealingly connecting to a scrubbing flow path comprising at least one gas conduit for removing the CD from the device. The gas conduit has fourth couplings for connecting the device to the scrubbing flow path.

In some embodiments, a method comprises joining a flexible tent film material to at least one panel having fittings for connecting to source and return gas conduits, so as to form a gas-tight tent around a device to be treated. The source and return gas conduits are connected to the fittings and to couplings of a portable source of gaseous chlorine dioxide (CD), so as to form a sealed CD generation flow path connecting the portable source to the tent. Gaseous CD is pumped from the source through the tent to treat the device. The gaseous CD is returned from the tent to the source.

In some embodiments, a method comprises connecting a source gas conduit and a return gas conduit to supply and return fittings of a device to be treated, and to couplings of a portable source of gaseous chlorine dioxide (CD), so as to form a sealed CD generation flow path connecting the portable source to the device. Gaseous CD is pumped from the source through the device. The gaseous CD is returned from the device to the source. The source and return gas conduits are connected to supply and return fittings of a portable scrubber to form a scrubbing flow path. The CD is removed from the device by pumping gas from the device through the scrubber. The scrubbed gas is returned from the scrubber to the device.

BRIEF DESCRIPTION OF THE DRAWINGS

FIG. 1B is a schematic diagram of the system of FIG. 1A, during operation in a $ClO_2$ scrubbing mode.

FIG. 3 is a drawing of the scrubber assembly of FIG. 1A.

DETAILED DESCRIPTION

Figure 1A:
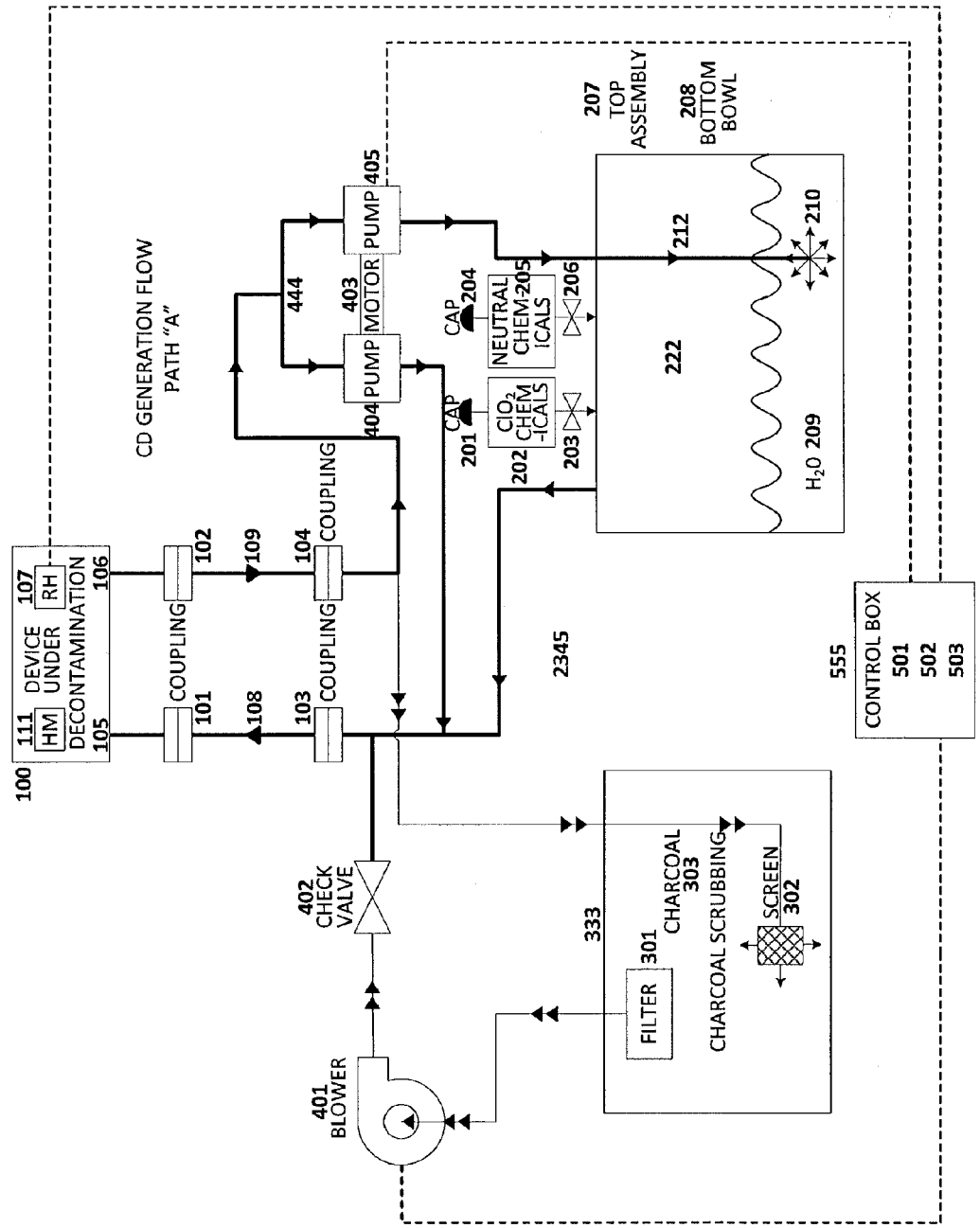
FIG. 1A is a schematic diagram of one embodiment, during operation in a $ClO_2$ generation mode.

This description of the exemplary embodiments is intended to be read in connection with the accompanying drawings, which are to be considered part of the entire written description. In the description, relative terms such as "lower," "upper," "horizontal," "vertical,", "above," "below," "up," "down," "top" and "bottom" as well as derivative thereof (e.g., "horizontally," "downwardly," "upwardly," etc.) should be construed to refer to the orientation as then described or as shown in the drawing under discussion. These relative terms are for convenience of description and do not require that the apparatus be constructed or operated in a particular orientation. Terms concerning attachments, coupling and the like, such as "connected" and "interconnected," refer to a relationship wherein structures are secured or attached to one another either directly or indirectly through intervening structures, as well as both movable or rigid attachments or relationships, unless expressly described otherwise.

One embodiment provides an apparatus and method to produce a gas for gaseous decontamination to reduce microorganisms thereon by treating a device (such as a BSC) or item(s) in a temporary enclosed sealed space or chamber. The apparatus includes a gas circulation loop, a means for providing gas introduction and removal, that is comprised of supply and return ducting with couplings connected to inlet and outlet ports affixed to respective sealing panels incorporated onto the device or temporary enclosed sealed space. The apparatus has a closed loop of gas-tight construction isolated from the ambient space.

The corresponding embodiment of a method comprises exposing the device or item(s) in a temporary enclosed sealed space or chamber to an atmosphere comprising gaseous chlorine dioxide. It may comprise controlling the concentration and required time cycles of chlorine dioxide generation, dwell and rapid removal. This embodiment of a method also provides the proper humidity to enhance the susceptibility of microorganisms and/or sporicidal action of chlorine dioxide. Neutralizer is added to the residual waste liquid within the apparatus, following which the waste liquid may be discarded by conventional or future developed means. The chlorine dioxide gas is produced from a precursor solid chemical, mixed into an aqueous solution, then transformed to a gaseous state. The method may also be used with larger devices or sealed spaces with additional quantities of Chlorine Dioxide generating chemicals. Additional items may be added to the space under decontamination.

Embodiments may take physical form in certain parts and arrangement of parts, a preferred embodiment of is described in detail below and illustrated in the drawings.

FIGS. 1A and 1B are schematic views of a Mini Chlorine Dioxide Generator (MCS) decontamination system 2345. MCS 2345 includes a source 222, a scrubber 333, and a controller 555. The system is capable of being operated in a chlorine dioxide (CD or $ClO_2$) generation mode or in a scrubbing mode. The CD generation mode flow path is shown in FIG. 1A. The scrubbing mode flow path is shown in FIG. 1B.

FIG. 1A shows a device under decontamination 100. In some embodiments, the device under decontamination 100 has its own supply and return gas ports, and is connected directly to supply 108 and return 109 gas conduits. In other embodiments, the device under decontamination 100 is surrounded by a gas tight tent 1502 (FIG. 15), which is in turn connected to the supply 108 and return 109 gas conduits.

A humidity source 107, humidity meter 111, and optional biological indicator (not shown) are placed within the decontamination zone. The device under decontamination 100 is then sealed, incorporating into the sealing panel a gas inlet 105 and outlet port 106 for use with the MCS 2345. In some embodiments, to accomplish the seal, the tent material is taped using a suitable pressure sensitive adhesive tape (such as duct tape) to a sealing panel (FIG. 16C) having the inlet port 105 and/or outlet port 106. After appropriate humidity has been achieved, Chlorine Dioxide ($ClO_2$) is produced and released and the decontamination cycle begins. FIG. 1B shows the apparatus with the CD scrubbing flow path activated. After a suitable exposure time (e.g, 85 minutes), $ClO_2$ gas is removed from the device under decontamination 100 using the scrubbing cycle of the MCS 2345. After a suitable scrubbing time (e.g., approximately 45 minutes), the MCS 2345 is disengaged from the device under decontamination 100 and may be unsealed.

FIGS. 1A and 1B show a Mini Chlorine Dioxide Generator (MCS) decontamination system 2345 using chlorine dioxide ($ClO_2$) gas. The MCS 2345 is affixed to a device or temporary enclosed sealed space 100 under decontamination. By way of example, and not limited, device 100 may take the form of a Class II type A1, A2, B1, and B2 biological safety cabinet (BSC), Class I BSC, Class III BSC, negative or positive isolators, animal devices, incubators, refrigerators and freezers, room or any other potentially contaminated item(s). The MCS 2345 may be used with devices or temporary enclosed sealed spaces having a volume of typically less than 120 ft$^3$ (3.4 m$^3$). The MCS 2345 may also be used with larger devices or sealed spaces with additional quantities of $ClO_2$ generating chemicals. Additional items may be added to the space under decontamination.

System 2345 includes a "closed loop" gas circulation system that is comprised of ducting connected between inlet port 101 and outlet port 102 of device or temporary enclosed sealed space 100. In the illustrated embodiment, the circulation system includes a supply ducting 108 and a return ducting 109. To seal or affix to the device or temporary enclosed sealed space 100 under decontamination, sealing panels 105, 106 are provided. In other embodiments, other panels (not shown) are incorporated for various configurations of the intake and return conduits for device or temporary enclosed sealed space 100. Quick disconnect couplings 101, 102, 103, 104 (which may include locking levers or other positive sealing mechanisms) connect the lines to the sealing panels 105, 106 or other sealing panels and to the MCS 2345.

The "closed loop" air circulation systems is defined in two flow paths "A" and path "B". Flow path "A" (indicated by the single arrow in FIG. 1A) is the $ClO_2$ Generation path, and flow path "B" (indicated by double arrows in FIG. 1B) is the $ClO_2$ scrubbing path.

Flow path "A" (FIG. 1A): $ClO_2$ generation and recirculation blowers or pumps 444 are included in the "closed loop" gas circulation system. The blower or pumps 444 are located within the gas circulation loop including the supply ducting 108 and return ducting 109 and MCS 2345. The $ClO_2$ blower or pump 444 is driven by a motor 403. In some embodiments, the blower or pump 444 has duel heads 404, 405, of which one provides air to the sparging tubing 212 in the dispensing assembly 222, and the second head in the "closed loop" provides additional airflow volume to circulate the $ClO_2$ gas and moisture (from humidity source 111) through the device under decontamination 100. In some embodiments, the blower or pump 444 is powered by the control box 555 with a dedicated switch 502, and both may be dual head suction pumps.

Flow path "B" (FIG. 1B): The $ClO_2$ scrubbing and recirculation blower 401 is included in the "closed loop" gas circulation system. The blower 401 is located within the gas circulation loop including the supply ducting 108 and return ducting 109 and MCS 2345. The $ClO_2$ scrubbing blower 401 is driven by a motor (not shown). The blower 401 is sized to provide a higher airflow volume than the $ClO_2$ blower or pump 444 to quickly scrub the $ClO_2$ gas from the device under decontamination 100. The blower 401 is powered by the control box 555 with a dedicated switch 501. To prevent backflow through the recirculation loop a check valve 402 is in line after the discharge of the blower 401.

A $ClO_2$ generator or dispensing assembly 222 is coupled to the supply ducting 108 and return ducting 109. $ClO_2$ generator 222 includes a top assembly 207, bottom bowl 208, caps 201,204, chemical dispensing tubes 202, 205 and chemical dispensing valves 203, 206 and sparging tubing 212. $ClO_2$ is generated within assembly 222 and delivered to the device or temporary enclosed sealed space 100.

Figure 2:
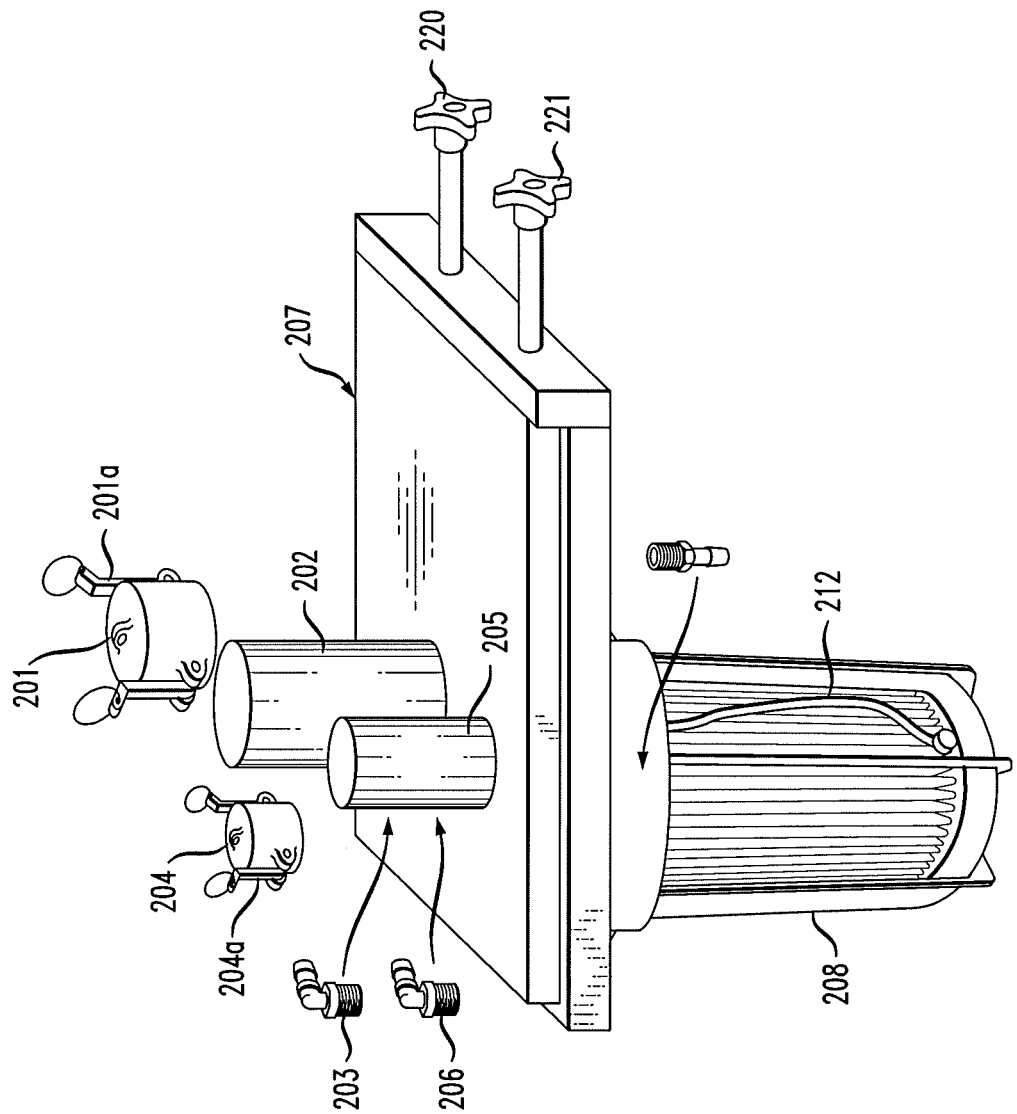
FIG. 2 is a drawing of the CD generation assembly of FIG. 1A.

FIG. 2 shows a $ClO_2$ generator or dispensing assembly 222 including a top assembly 207 and bottom bowl 208. The bottom bowl 208 is removable to add the predetermined quantity of $H_2O$ 209 and replaced using a bowl wrench (not shown) and a gas tight "O" ring. Two gas tight caps 201, 204 are placed on top of the two chemical dispensing tubes 202, 205. The caps 201, 204 are removed and then replaced with locking levers 201a, 204a to add the appropriate amount of $ClO_2$ generating and $ClO_2$ neutralizing chemicals. Within each of the two chemical dispensing tubes 202, 205 is a chemical dispensing valve 203 and 206 to release the $ClO_2$ generating and neutralization chemicals at the predetermined time, without any chemical release or leakage from the MCS 2345, The valves 203, 206 are actuated by handles 220, 221, respectively. Within the bottom bowl 208, sparging tubing 212 with air dispensing unidirectional exit holes 210, is run within the closed air circulation loop, wherein $ClO_2$ is generated and delivered to the device or temporary enclosed sealed space 100. The chlorine precursor material may be, for example, sodium chlorite. The neutralizing chemical may include, for example, sodium thiosulfate, an inorganic base (e.g., sodium hydroxide), and/or a high pH buffer. Other scrubbing chemicals may include sulfur dioxide, hypochlorite, or a white liquor containing NaOH, $Na_2CO_3$, and $Na_2SO_4$. In some embodiments, a mixture of sodium bicarbonate and sodium thiosulfate sold under the product name "MCS Neutralizer Powder" by DRS Laboratories of Lehigh Valley, Pa. may be used.

Figure 2A:
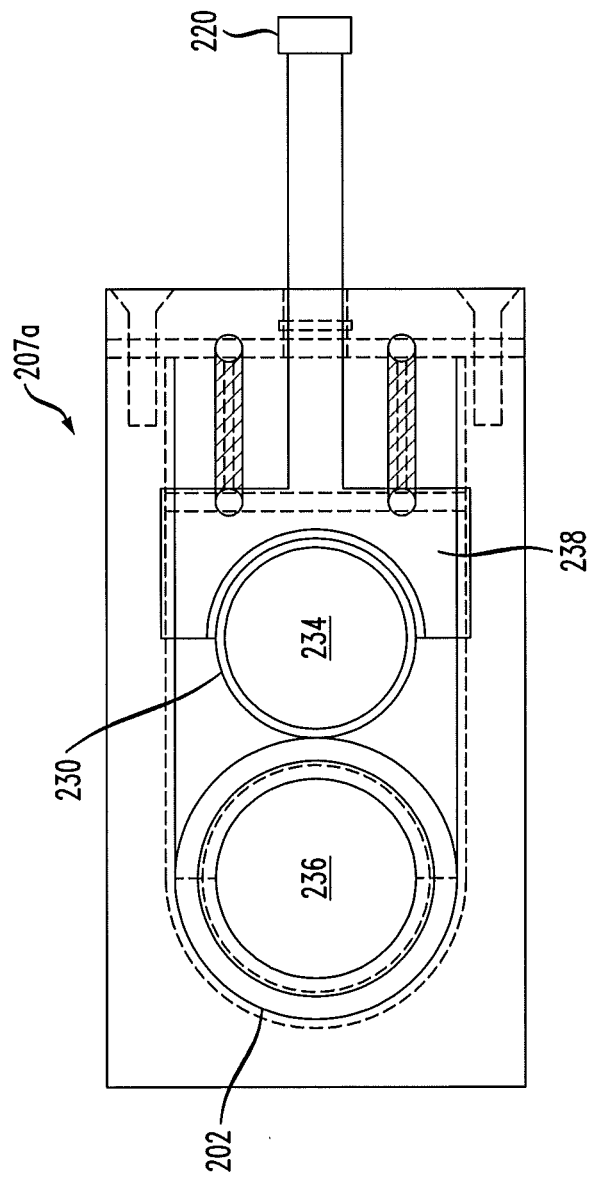
FIG. 2A is a plan view of one of the CD precursor dispensers of FIG. 2.

FIG. 2A is a plan view of one dispenser 207a of the top assembly 207, for dispensing the $ClO_2$ precursor. A similar dispenser unit in top assembly 207 dispenses the neutralizing chemical. The dispenser 207a includes a cylindrical well 230 for receiving a quantity of the solid $ClO_2$ precursor. Dispenser 207a has a dispensing damper 238 slidably mounted therein. When the cylindrical well 230 overlies a solid planar surface 234 of the dispenser 207a, the well 230 holds the solid material. When the handle 220 is actuated to move the well 230 of damper 238 into alignment with the opening 236 of dispensing tube 202, a complete vertical path is formed, through which the solid material drops into the bottom bowl 208.

FIG. 3 shows a $ClO_2$ charcoal scrubber 333 incorporated in the supply ducting 108 and return ducting 109. $ClO_2$ charcoal scrubber 333 includes a inlet screen 302 (which may be a foot valve screen), outlet filter 301 with associated piping, wherein $ClO_2$ is removed from the device or temporary enclosed sealed space 100. The $ClO_2$ charcoal scrubber 333 includes a unidirectional inlet screen 302 with associated piping to draw the $ClO_2$ gas into the charcoal bed 303 at the base of the scrubber 333. At the top of the charcoal bed 303 is an outlet filter 301 with associated piping, wherein $ClO_2$ is filtered prior to removed from scrubber 333.

Referring again to FIGS. 1A and 1B, the MCS 2345 includes a Control Box 555. In some embodiments, there are three circuit breaker switches 501, 502, 503 to control the system, and three LED's (not shown) with visual illumination to indicate which cycle is in use. In some embodiments, the blower 401 is powered by dedicated switch 501, blower or pump 444 is powered by dedicated switch 502, and steam generator (RH) 107 is powered by dedicated switch 503.

In accordance with the illustrated embodiment, device or temporary enclosed sealed space 100 includes a humidity source (e.g., a steam generator) 107 to provide the proper amount of humidity (RH) to perform a acceptable decontamination in conjunction with the required amount of $ClO_2$ gas. The RH generator 107 is placed within the device or temporary enclosed sealed space 100 under decontamination, power is supplied by a power cord incorporated within the supply sealing panel 105. The power cord is plugged into and powered by the control box 555 with a dedicated switch 503.

To measure the RH a RH meter 111 is placed within the device or temporary enclosed sealed space 100.

Figure 15:
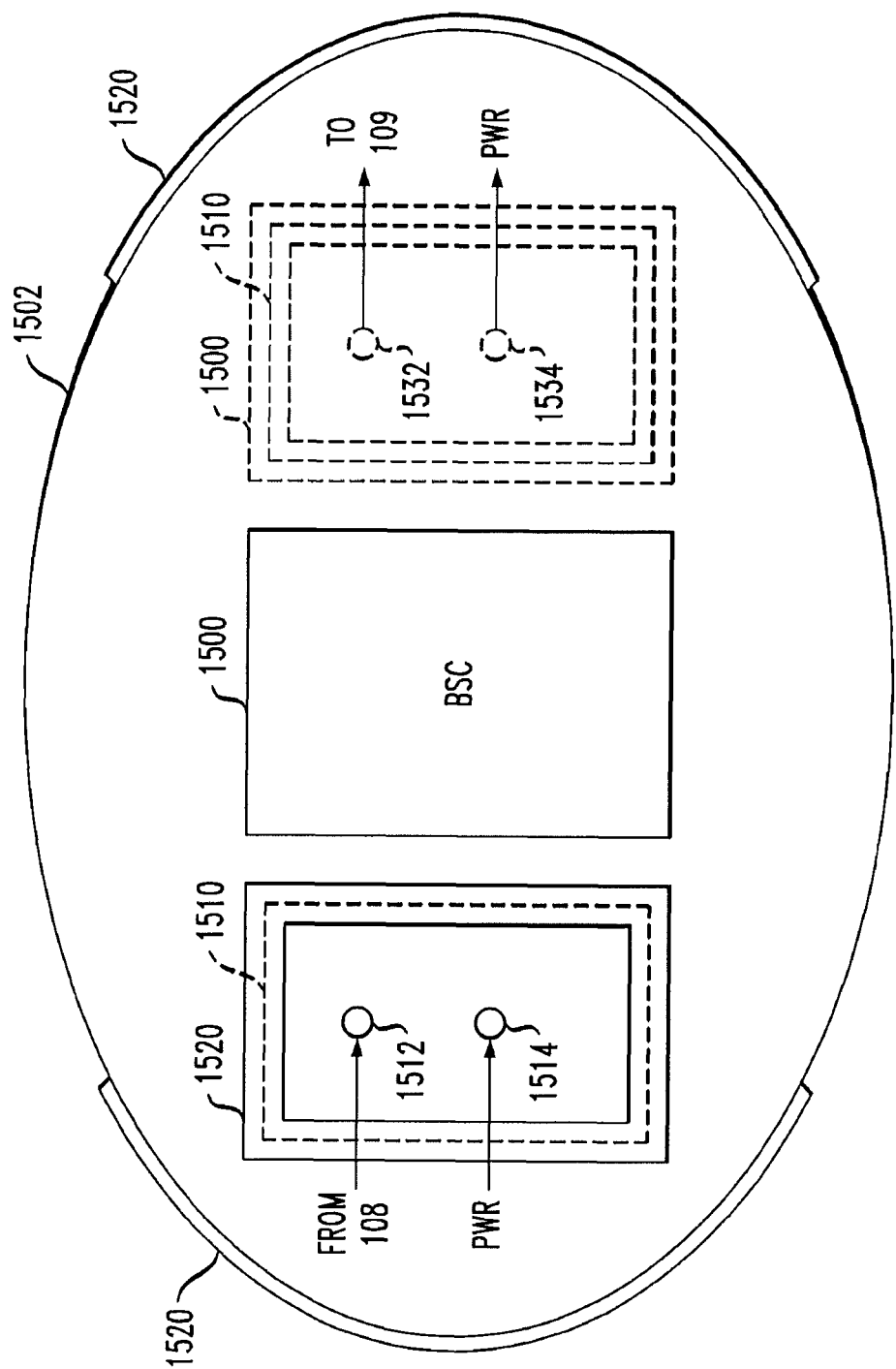
FIG. 15 is a schematic diagram of a tent structure with sealing panels, for containing the device to be contaminated.

FIG. 15 shows a tent structure 1502 that can be formed of a variety of gas impermeable polymer films, such as for example, 0.004 inch polyvinyl chloride (which may be transparent). The tent structure 1502 may be formed from a flat sheet of the polymer material, and sealed in any desired shape so as to enclose the device 1500 to be decontaminated using a pressure sensitive adhesive tape, such as duct tape 1520, or the like. Source panel 1510 and return panel 1530 are also sealed to the tent material using a pressure sensitive adhesive tape, such as duct tape 1520, or the like.

In some embodiments, the source panel 1510 and return panel 1530 are formed from sheets of polymer such as flat, transparent 0.04 inch PVC film. The panels may be 24" by 30", but other sizes may also be used. The material of panels 1510 and 1530 is selected to have sufficient structural integrity to support the gas tight fittings 1512 (for gas source) and 1512 (for gas return). In some embodiments, the panels have also have optional fittings 1514, 1534 for passing a power cord into the tent structure 1502, for example to operate the humidity source 107. The panels 1510 and 1530 can easily be joined to a polymer tent material with pressure sensitive adhesive tape, allowing the use of tent materials that have great flexibility, without requiring the tent material to be capable of supporting the connectors.

Figure 16B:
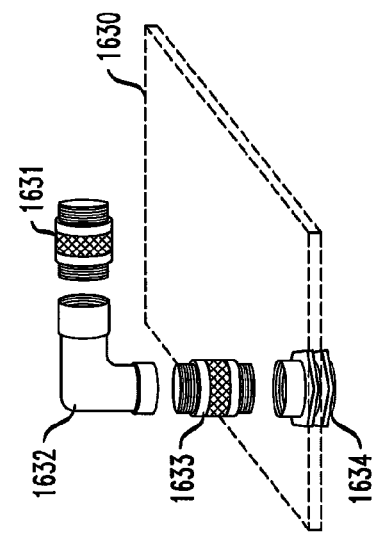
FIGS. 16A-16C show various sealing panels that may be used in the system of FIG. 1A.
Figure 16C:
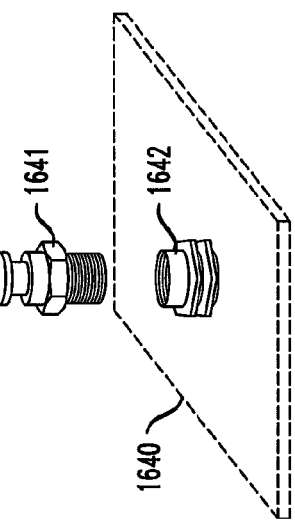
Figure 16A:
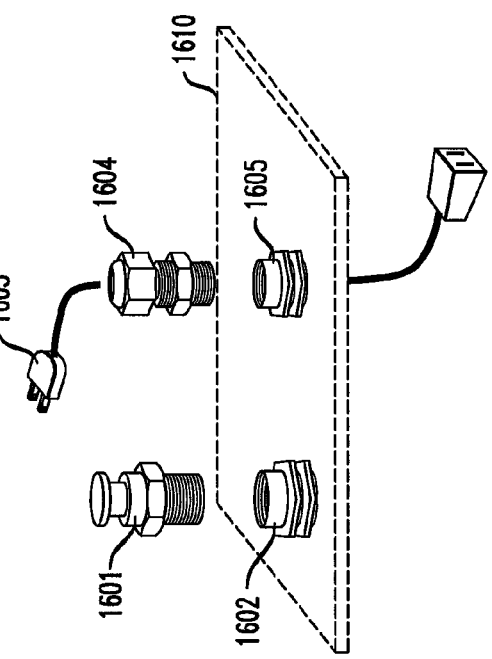

FIGS. 16A to 16C show exploded views of three exemplary sealing panels, to reveal exemplary fittings. FIGS. 16A and 16B show standard equipment sealing panels, and FIG. 16C shows a tenting panel. In some embodiments, The coupling is connected to the sealing panel(s) AND then the sealing panel(s) are taped to the BSC, so that the coupling does not get directly connected to a conduit in the BSC. Because the exemplary panels can be joined to the BSC or tent structure with adhesive tape, they provide a one-size-fits-all solution for forming gas-tight connections between the device/tent structure and the MCS 2345.

In FIG. 16A, an exemplary supply line sealing panel 1610 includes a cam and groove hose coupling plug (e.g., male) adapter 1601, through wall fittings (e.g., female) 1602, 1605 for gas and power, respectively, and cord grip 1604. This panel is suitable for use connection to various BSC types.

In FIG. 16B, the exemplary return line is outfitted for supporting the gas line, without the optional plug. Panel 1630 has a threaded pipe fitting 1633 and through wall fitting 1634. Fittings 1631 and 1632 are included to accommodate the gas line configuration. Preferably, the connector 1631 is a cam and groove hoe coupling allowing for quick connect and disconnect. This panel is suitable for use connection to various BSC types.

In FIG. 16C, a panel is provided for joining to a tent material that surrounds a device to be decontaminated (as shown in FIG. 15). For this purpose, a smaller panel (e.g., 12"×12" may be used. In the example of FIG. 1C, a cam and groove hose coupling 1641 with female adapter and a polyethylene through wall fitting 1642 are included. In this embodiment, no fitting is provided for a power cable.

Figure 4:
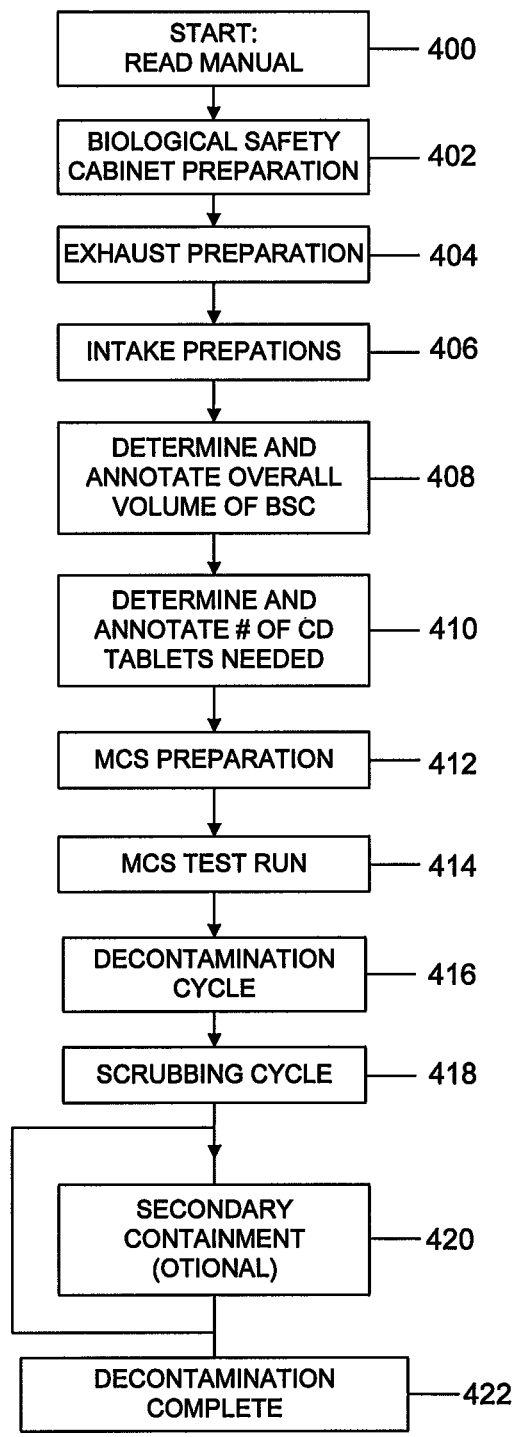
FIG. 4 is a top level flow diagram of a method of using the system of FIG. 1A.

FIG. 4 is a high level flow chart of a process for performing a decontamination of a Class II Type A1, A2, B1, B2 Biological Safety Cabinet (BSC) 100. When the system of FIGS. 1A and 1B is applied to other devices, slight modifications on attachment, sealing and circulation are applied, as will be apparent to one of ordinary skill. For example, in other embodiments, the device to be decontaminated is not a BSC, and a tent material is placed around the device, and sealed to appropriate sealing panels described herein, using a pressure sensitive adhesive tape (e.g., duct tape). The gas conduit connections to the ports of the sealing panels can be made in the same manner as connecting the conduit to the BSC. In addition, a power cord for the humidity generator 107 can be passed through an opening or fitting in the sealing panel and a gas-tight seal formed around the cord.

Referring again to FIG. 4, at step 400, prior to using the system, the user reviews the manual and safety procedures.

At step 402, the BSC 100 is prepared. Details of this step are discussed below with reference to FIG. 5.

At step 404, the exhaust preparations are performed. Details of this step are discussed below with reference to FIG. 6.

At step 406, the intake preparations are performed. Details of this step are discussed below with reference to FIG. 7.

At step 408, the overall volume of BSC 100 is determined and annotated.

At step 410, the amount of CD precursor (e.g., number of tablets or pellets, or volume of powder) is determined and noted. Details of this step are discussed below with reference to FIG. 8.

At step 412, the MCS 2345 system is prepared. Details of this step are discussed below with reference to FIG. 9.

At step 414, a test run is performed using the MCS 2345. Details of this step are discussed below with reference to FIG. 10.

At step 416, the decontamination cycle is performed. Details of this step are discussed below with reference to FIG. 11.

At step 418, the scrubbing cycle is performed. Details of this step are discussed below with reference to FIG. 12.

At step 420, an optional secondary containment step is performed. Details of this step are discussed below with reference to FIG. 13.

At step 422, the decontamination is complete, and a post-decontamination procedure is performed. Details of this step are discussed below with reference to FIG. 14.

Figure 5:
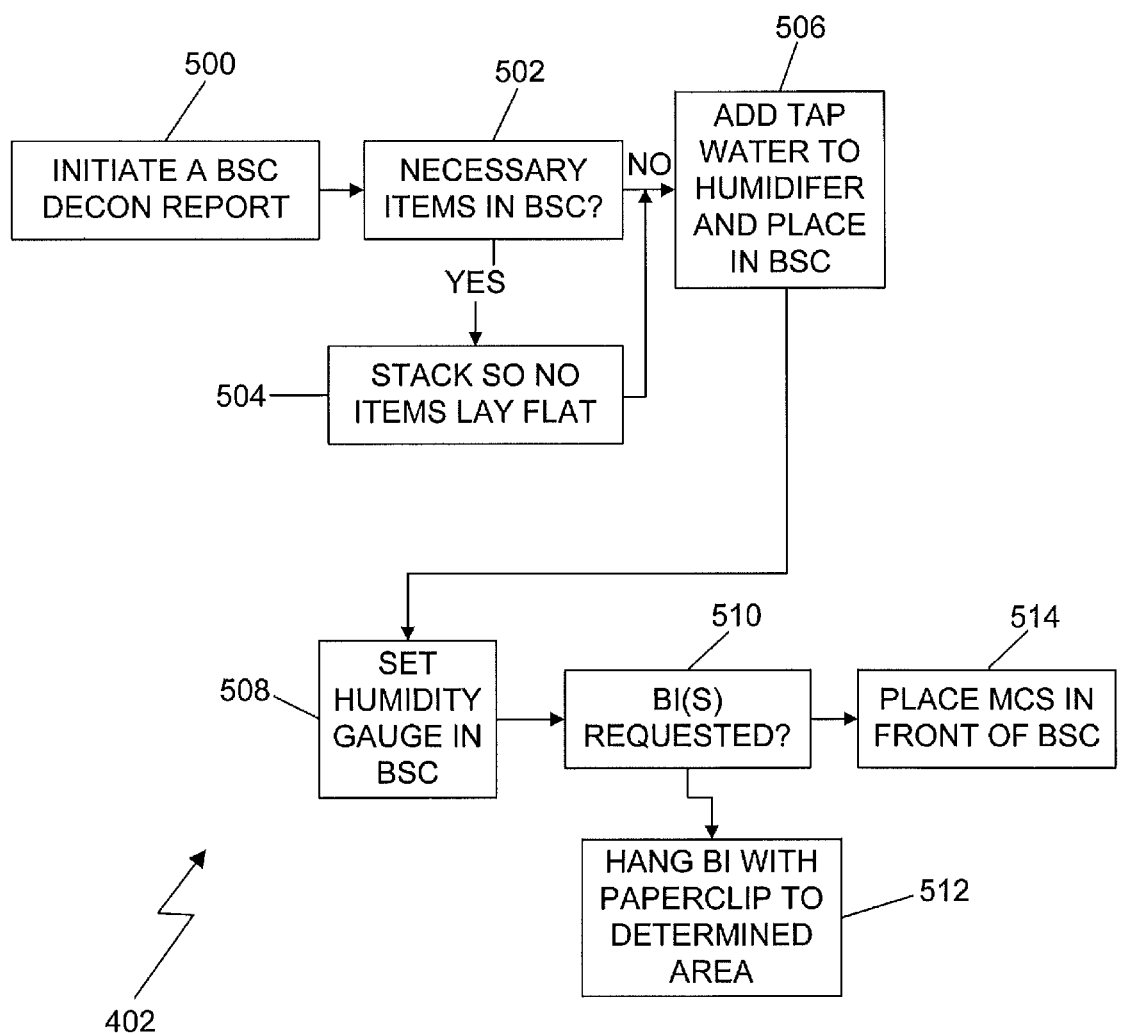
FIG. 5 is a flow chart of the BSC preparation process of FIG. 4.

Referring to FIG. 5, the BSC Preparation is shown.

At step 500, a BSC decontamination report (i.e. . . . Manufacturer, model number, serial number, volume, etc. . . . ) is initialized.

At step 502, the user verifies that only items to be decontaminated are within the BSC.

At step 504, the user verifies that all items remaining in the BSC are stacked in a way that the humidity and $ClO_2$ gas can contact all surfaces, and no items lay flat or obstructed. If items require power, they are plugged into the BSC's receptacle and tested for operation ensuring the current draw does not exceed the rated capacity of the BSC's receptacle(s). The BSC may be prepped or moved such that appropriate sealing will be possible (e.g., in animal areas where the BSC units are on casters).

At step 506, the user removes the cap and adds tap water to hand held humidifier to a depth of ½ way up the sight glass. The user replaces the cap and inserts it into the BSC. A sight glass visible fill line may be provided to assist the user in determining a maximum fill height.

At step 508, the user sets or affixes a humidity gauge within the volume to be decontaminated. The ideal placement of the gauge within a laminar flow BSC is on the front grill toward the left hand side of the unit. The user ensures that the gauge will be visible during the decontamination and that there is unimpeded flow through the front and/or back of the gauge. If using a wireless remote humidity gauge, the user ensures that the monitoring station can read the remote.

At step 510, a determination is made whether a biological indicator (BI) was requested.

At step 512, if requested, the user can optionally affix at least one biological indicator (BI) within the BSC(s) at a pre-determined location(s). If using a BI with a Tyvek envelope, the user pushes a hanger (e.g., an opened paperclip or other hanger) through one end of the Tyvek envelope, and then attaches the hanger to an internal surface of the BSC. If the hanger cannot be directly hung, the surface is decontaminated with the appropriate disinfectant or sterilant, ensuring proper contact time prior to affixing the tape.

At step 514, the user places the MCS 2345 in front of the BSC. The user ensures that all power switches are off and plug in the unit.

Figure 6:
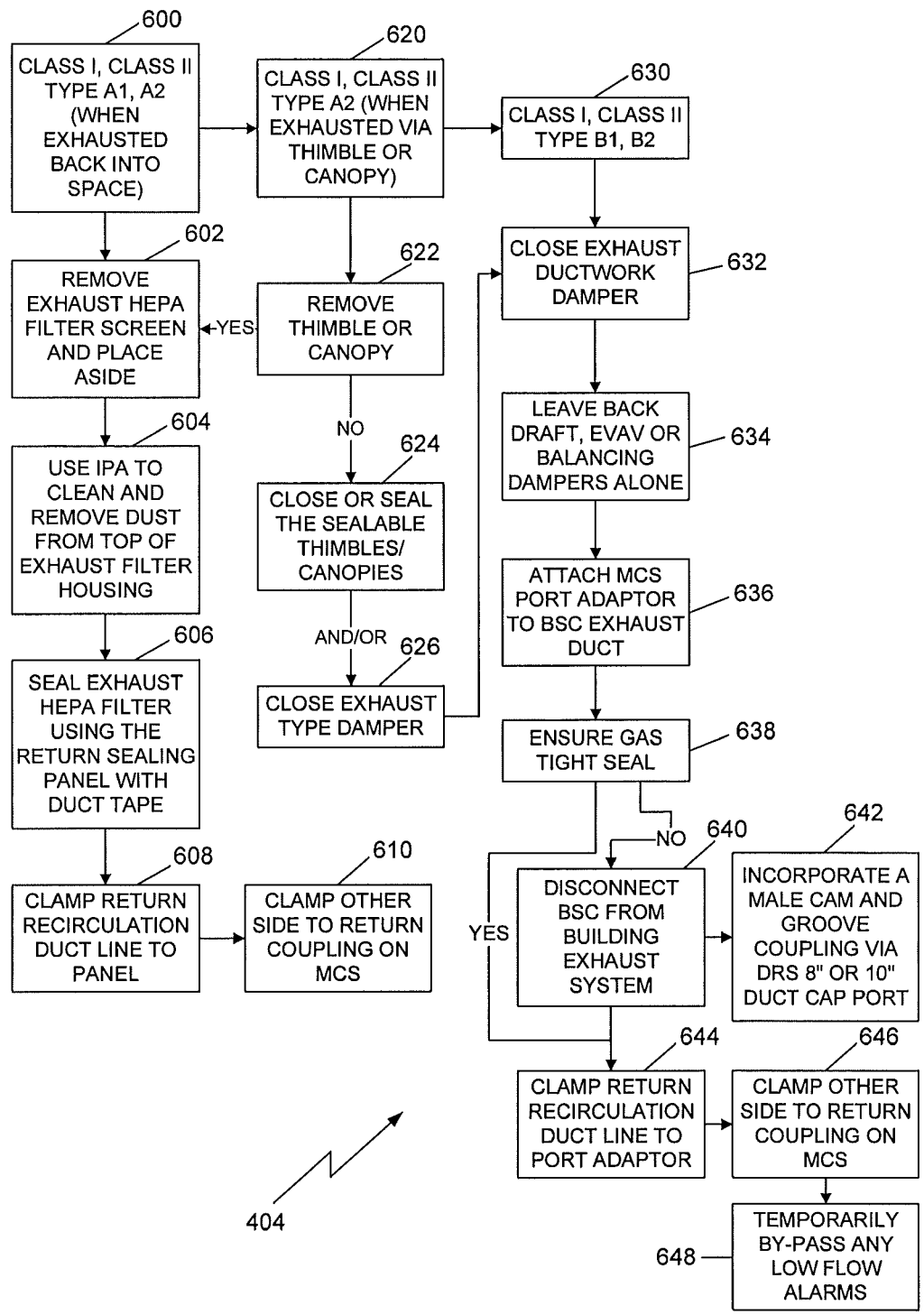
FIG. 6 is a flow chart of the exhaust preparation process of FIG. 4.

FIG. 6 shows the exhaust preparation step. Exhaust preparation of various classifications use different exhaust sealing configurations, as follows:

At step 600, steps 602-608 are performed for Class I, Class II Type A1, A2 (when the gas in the system (after completion of the scrubbing cycle) is exhausted back into the space).

At step 602, the user removes the exhaust HEPA filter protective screen and places it aside.

At step 604, the user uses isopropyl alcohol (IPA) or other cleaning solvents to clean and remove dust or debris from the top exhaust filter housing.

At step 606, the user seals the exhaust HEPA filter using a return sealing panel (which may be configured with male cam and groove coupling) using duct tape or other sealing material.

At step 608, the user clamps the return recirculation duct line with a corresponding coupling on the return sealing panel (e.g., connecting a locking female cam and groove coupling on the duct line to a male cam and groove coupling on the return sealing panel).

At step 610, the user clamps the other end of the recirculation duct line (which may for example, be equipped with a locking cam and groove coupling) to the return coupling of the MCS 2345. The return recirculation line may be affixed in either flow direction.

At step 620, steps 622-262 are performed for Class I, Class II Type A2 (when exhausted via thimble or canopy).

At step 622, the user removes the thimble or canopy. Thimble or canopy connections are spelled out in the National Sanitation Foundation (NSF International) Standard No. 49 for Class II (Laminar Flow) Biohazard Cabinetry, for connecting BSC to exhaust systems. This type of connection provides an air gap as to compensate for room pressurization changes.

Alternatively, at step 624, the user closes or seals the sealable type thimbles, canopies, and/or at step 626, the user closes the exhaust gas tight damper and follow the B1 or B2 procedure dependant on the sealing, and or, damper location relative to the exhaust HEPA filter. The user ensures that this is indeed a gas tight damper with no by-pass leakage. The user temporarily by-passes any low flow alarms.

At step 630, steps 632-648 are performed for a Class I, Class II Type B1, B2 BSC.

At step 632, the user fully closes the exhaust ductwork gas tight decontamination exhaust damper.

At step 634, the user leaves the back draft, EVAV or other balancing damper(s) in their original position.

At step 636, the user proceeds to affix a cam and groove male ductwork port or MCS port adaptor to the BSC's exhaust ducting prior to the gas tight damper.

At step 638, a determination is made whether this is indeed a gas tight damper with no by-pass leakage. In some embodiments (e.g., using a male cam and groove coupling ductwork adaptor, soft wall tubing and hose clamp to the port), duct tape or other sealing materials in particular should be checked to verify a gas tight seal. If there is not gas tight seal, step 640 is performed next. If there is a gas tight seal, 644 is performed next.

At step 640 If the BSC exhaust ducting does not have a seal or has a damaged gas-tight decontamination damper, the user disconnects the cabinet from the building exhaust system and step 642 is performed.

At step 642, the user forms a gas tight seal incorporating a male cam and groove coupling via DRS 8" or 10" duct cap port.

If step 638 determines that there is a gas tight seal, then step 644 is performed.

At step 644 the user clamps the return recirculation duct line with locking female cam and groove couplings to the male can and groove coupling on the biological safety cabinets exhaust duct port.

At step 646 the user clamps the other end of the recirculation duct line with the locking cam and groove coupling to the return coupling of the MCS. The return recirculation line may be affixed in either flow direction.

At step 648, the user temporally bypasses any low flow alarms to allow the recirculation blower in type B1 (B2 the MCS re-circulates the air) to operate.

Figure 7:
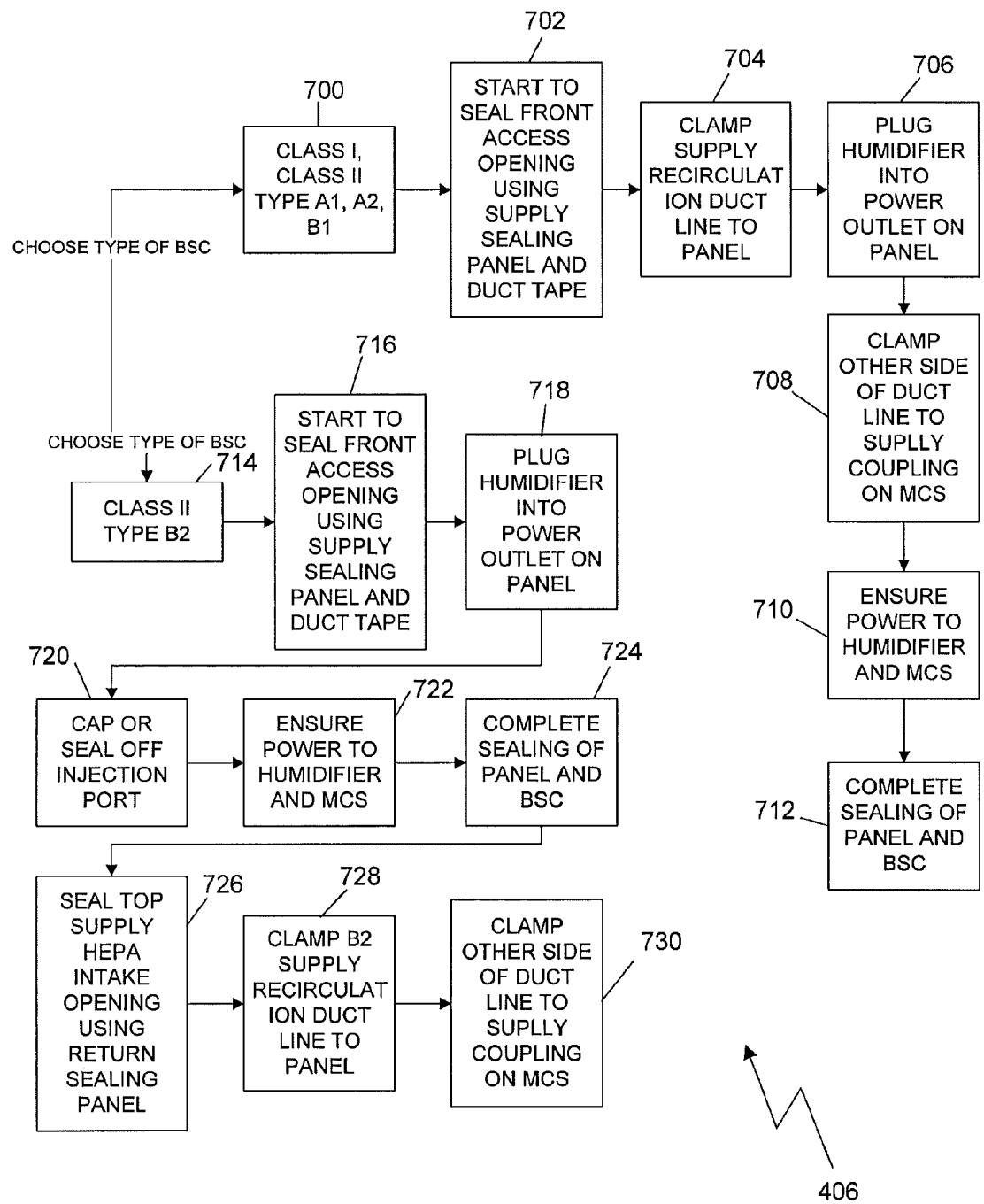
FIG. 7 is a flow chart of the intake preparation process of FIG. 4

FIG. 7 is a flow chart showing intake preparation of classifications. Steps 700-712 are performed for a Class I, Class II Type A1, A2, or B1 BSC. Steps 714-730 are performed for Class II Type B2 BSC.

At step 700, preparation starts for a Class I, Class II Type A1, A2, or B1 BSC.

At step 702, the user starts to seal the front access opening using the supply sealing panel with the male cam and groove coupling using duct tape or other sealing materials.

At step 704, once the sealing panel is partially secured, the user clamps the supply recirculation duct line with locking female cam and groove couplings to the male cam and groove coupling.

At step 706, the user plugs a humidification device into power outlet that is penetrating the sealing panel.

At step 708, the user clamps the other end of the recirculation duct line with the locking cam and groove coupling to the supply coupling of the MCS.

At step 710, prior to the final sealing of the front access opening, the user ensures there is power at the humidifier. The user plugs in the power cord to the receptacle located on the top of the control box. The user depresses the humidification "ON" switch to ensure there is power at the humidifier. In some embodiments, this is verified by three illuminated indicators.

At step 712, the user completes the final sealing of the panel and any other areas of the BSC.

At step 714, intake preparation for a Class II Type B2 is begun.

At step 716, the user starts to seal the front access opening using the supply sealing panel, using duct tape or other sealing materials.

At step 718, once the sealing panel is partially secured, the user plugs the humidifier's power cord into the extension cord that is affixed to the sealing panel. Once complete, the user plugs in the power cord to the receptacle located on the top of the control box.

At step 720, the user caps or seals off the injection port by covering it with duct style tape.

At step 722, prior to the final sealing of the front access opening, the user ensures there is power at the humidifier. The user activates the humidification "ON" switch to ensure there is power at the humidifier. In some embodiments, this will be verified by three illuminated indicators. Once this is verified, the user turns of the humidification switch. During this time the water will not have substantially heated within the humidifier.

At step 724, the user completes the final sealing of the panel and any other areas of the BSC.

At step 726, the user seals the top supply HEPA intake opening using the return sealing panel (dual purpose panel for this style B2 cabinet, actually used as the supply HEPA sealing panel in this application) with the male cam and groove coupling.

At step 728, the user clamps the B2 supply recirculation duct line with locking female cam and groove to the male cam and groove coupling on the sealing panel.

At step 730, the user clamps the other end of the B2 supply recirculation duct line with locking female cam and groove couplings to the supply coupling of the MCS. The B2 supply return recirculation line may be affixed in either flow direction. When clamping any cam and groove coupling together the user ensures the units "lock" The user ensures that the humidity gauge remains visible or if using a wireless remote humidity gauge, the monitoring station is reading the remote. The user determines and records the overall volume contained by the BSC enclosure.

Figure 8:
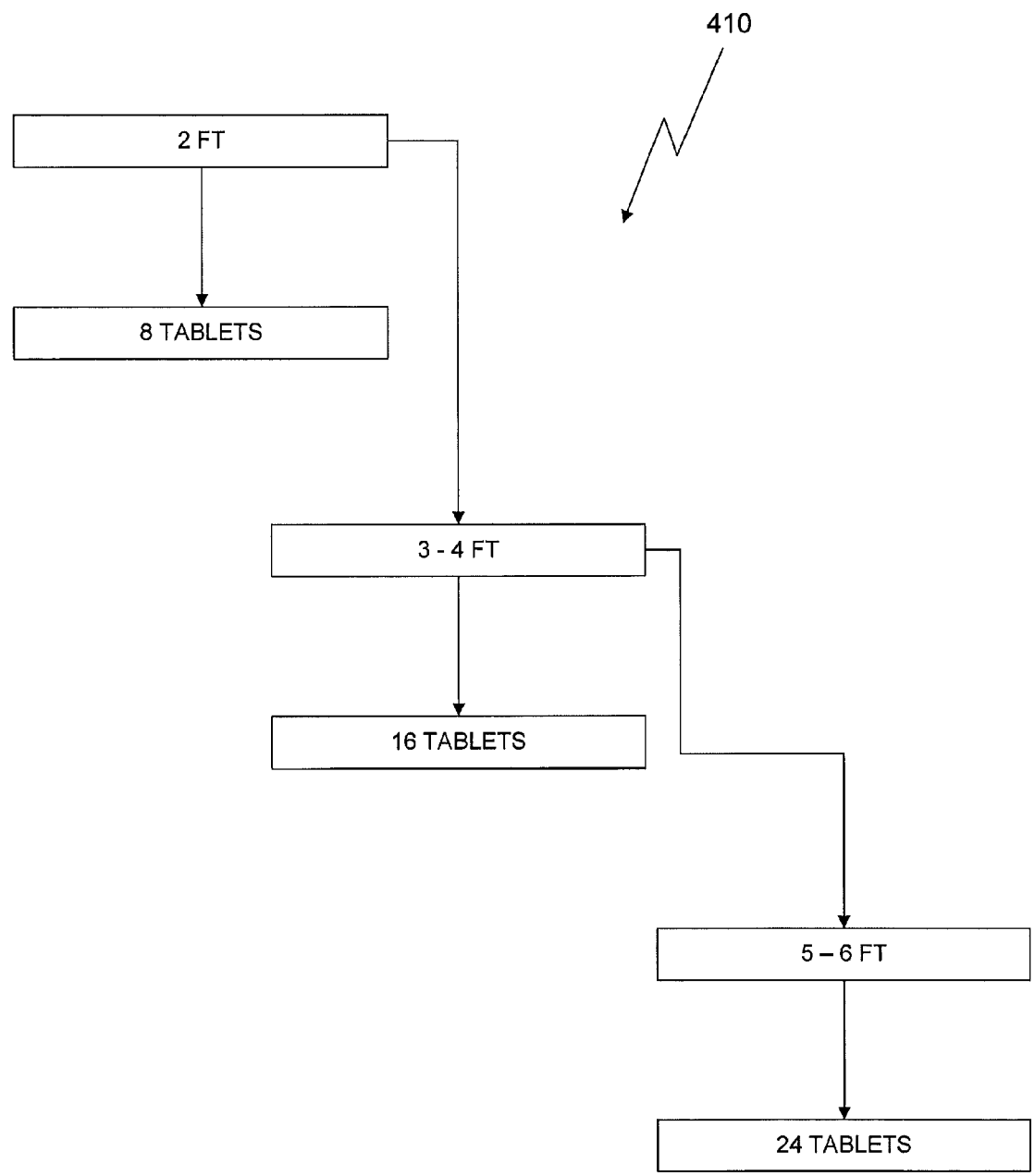
FIG. 8 is a flow chart of determining the amount of CD solids of FIG. 4.

FIG. 8 shows the process by which the user determines and notes the number of $ClO_2$ generating tablets to be used for the decontamination.

The user multiplies the BSC volume by 0.13 g/ft3 (4.7 g/m3) to determine the mass of $ClO_2$ required to be generated. Then, the user multiplies the $ClO_2$ mass by the unit mass of the supplied chemical generating tablets. The following table determines the amount of tablets (e.g., sodium chlorite) required. 79.5 mg of CD produced per gram of CD generating tablet or powder (tablet is 6 grams each) Need 0.13 g CD/ft3 of space being deconed. For example: a 6 foot BSC is 85 ft3×0.13=11.05 CD required. 24 tablets×6 gm tablet×0.0795 gm CD=11.4 g CD.

TABLE 1

| Minimum Volume - ft³ (m³) | Maximum Volume - ft³ (m³) | BSC Size Width - ft (m) | Chlorine Dioxide Generating Tablets |
|---|---|---|---|
| 0 (0) | 40 (1.1) | 2 ft (0.6) | 8 |
| 40 (1.1) | 60 (1.7) | 3-4 ft (0.91-1.22) | 16 |
| 60 (1.7) | 85 (2.4) | 5-6 ft (1.52-1.83) | 24 |
| 85 (2.4) | 120 (3.4) | Not applicable | 32 |

Figure 9:
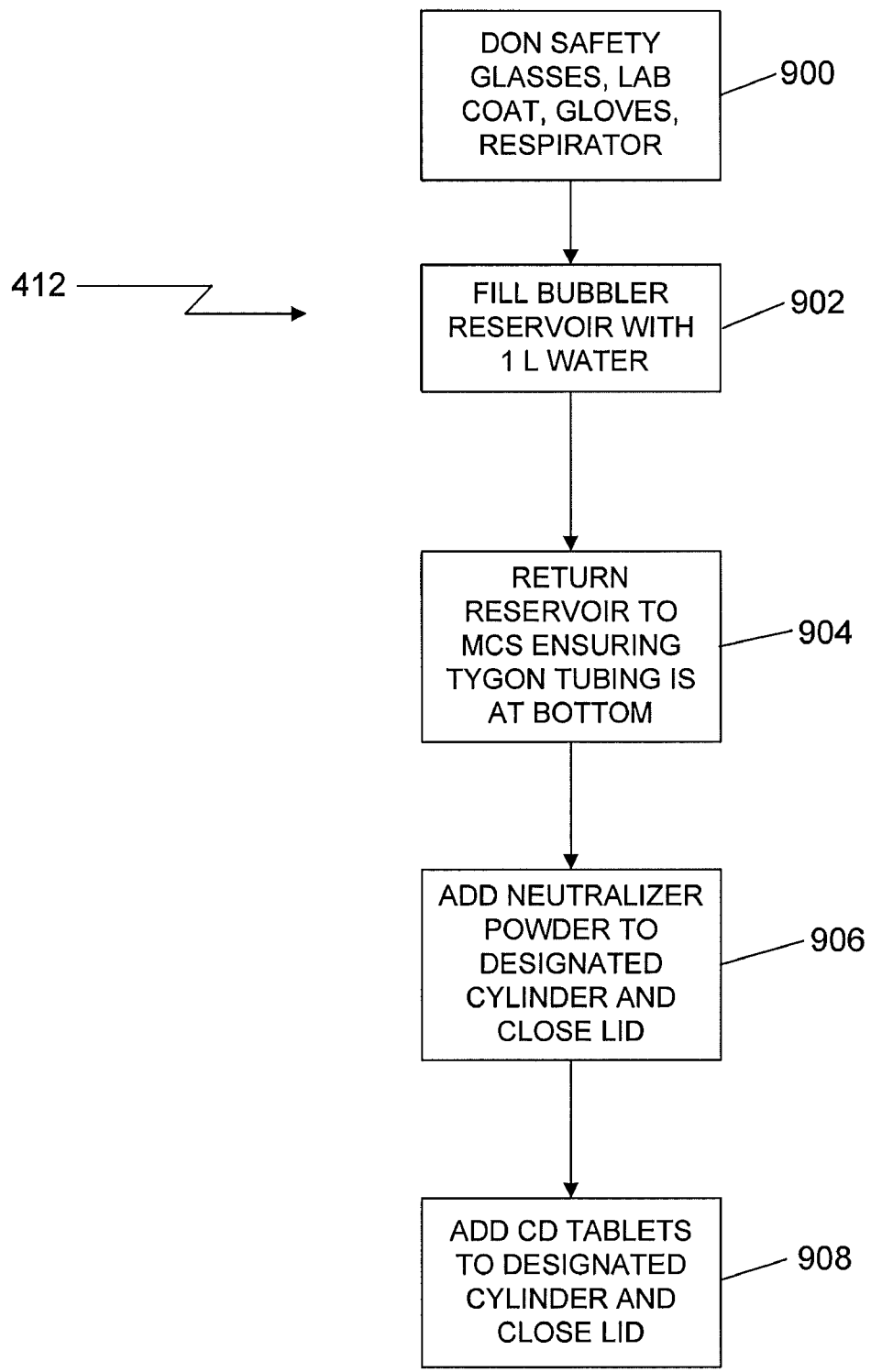
FIG. 9 is a flow chart of the mini-CD system (MCS) preparation process of FIG. 4.

FIG. 9 shows the Mini-CD System Preparation.

At step 900, the user dons safety glasses, lab coat, gloves and an appropriate respirator.

At step 902, the user starts setting up the MCS by first attaching, if not completed yet, the coupling on the supply line to the corresponding sealing panel on the BSC. Then, the user attaches the other end of the line to the MCS.

At step 904, the user attaches the return line to the sealing panel on the BSC. Then, the user attaches the other end of the line to the MCS. The user unthreads the bubbler reservoir and fill with tap water (e.g., 1 liter room temperature water). The user wipes off any splashes on the exterior of the reservoir. The user threads the bubbler reservoir up into the $ClO_2$ dispensing assembly, ensuring that the internal tygon tubing is hanging to the bottom of the reservoir. Prior to threading, the user ensures that an o-ring gasket is in place and there is a slight film of high vacuum grease on the gasket.

At step 906, the user removes the cap from Neutralizer dispensing cylinder. The user verifies the slide damper is closed and fills the pre-measured neutralizing powder mixture into the cylinder. The user places the cap back on top of cylinder and make sure levers are fully locked into place.

At step 908, the user removes the cap from $ClO_2$ dispensing cylinder. The user verifies the slide damper is closed 100%. The user fills a pre-determined number of tablets (Table 1) into the cylinder. The user places the cap back on top of cylinder and makes sure the cap is fully locked into place.

Figure 10:
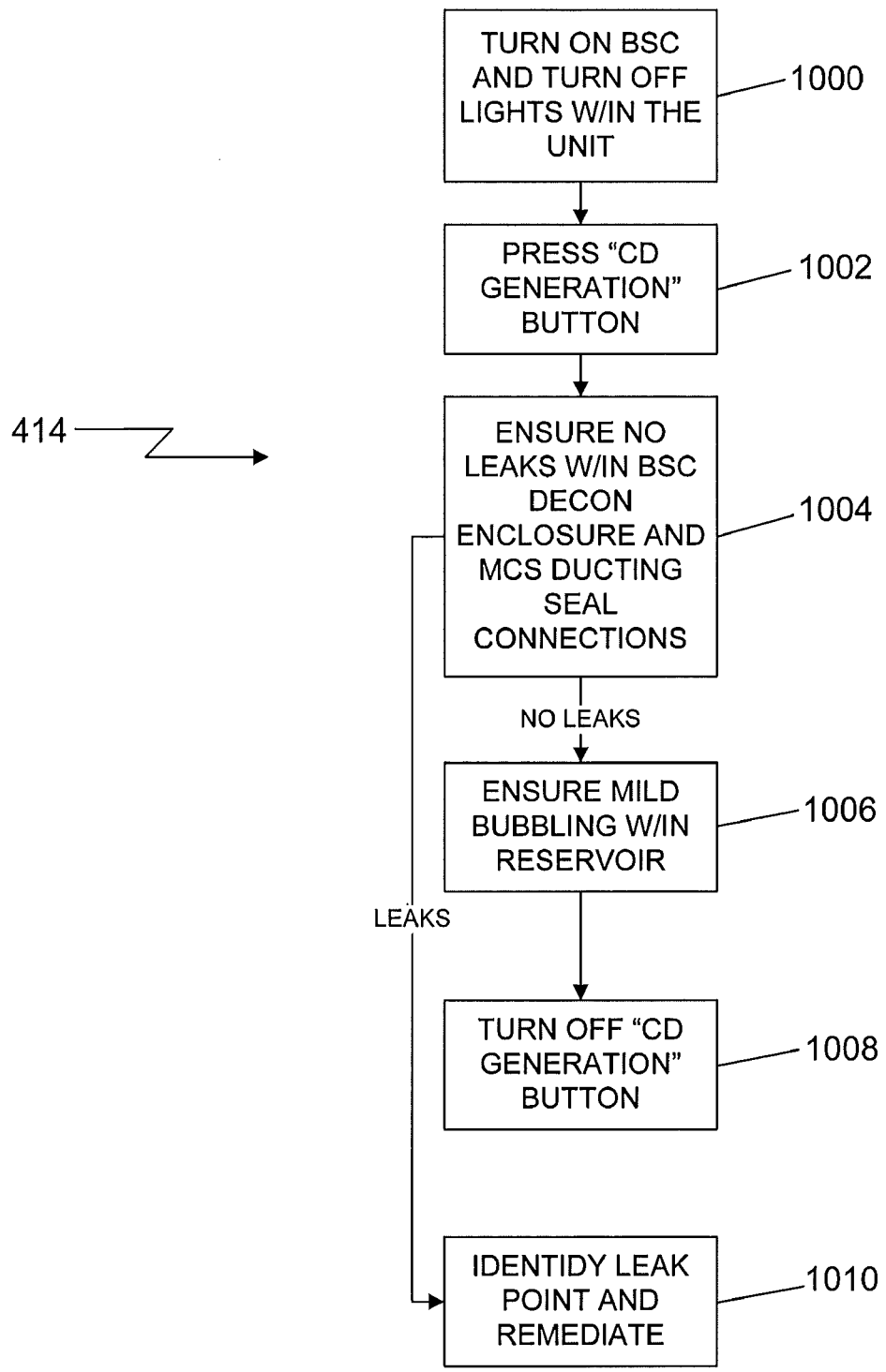
FIG. 10 is a flow chart of the MCS test run process of FIG. 4.

FIG. 10 shows a procedure for an MCS Test Run

At step 1000, the user turns on the BSC.

At step 1002, the user activates the switch on the control box to intiate CD Generation, in order to energize the recirculation pump.

At step 1004, the user ensures that there are no significant leaks within the BSC decontamination enclosure or MCS ducting seal connections by observing all the sealing material and connections that comprise the enclosure. In some embodiments, a 2-5 minute test run is sufficient. If there is a leak, step 1010 is performed.

At step 1006, the user ensures there is a mild bubbling within the reservoir, indicating that sparging is in process for CD generation.

At step 1008, the test run is complete, and the user turns off the CD generation.

At step 1010, if the enclosure does not appear relatively neutral in pressure, the user identifies the leak point and remediates the situation.

Figure 11:
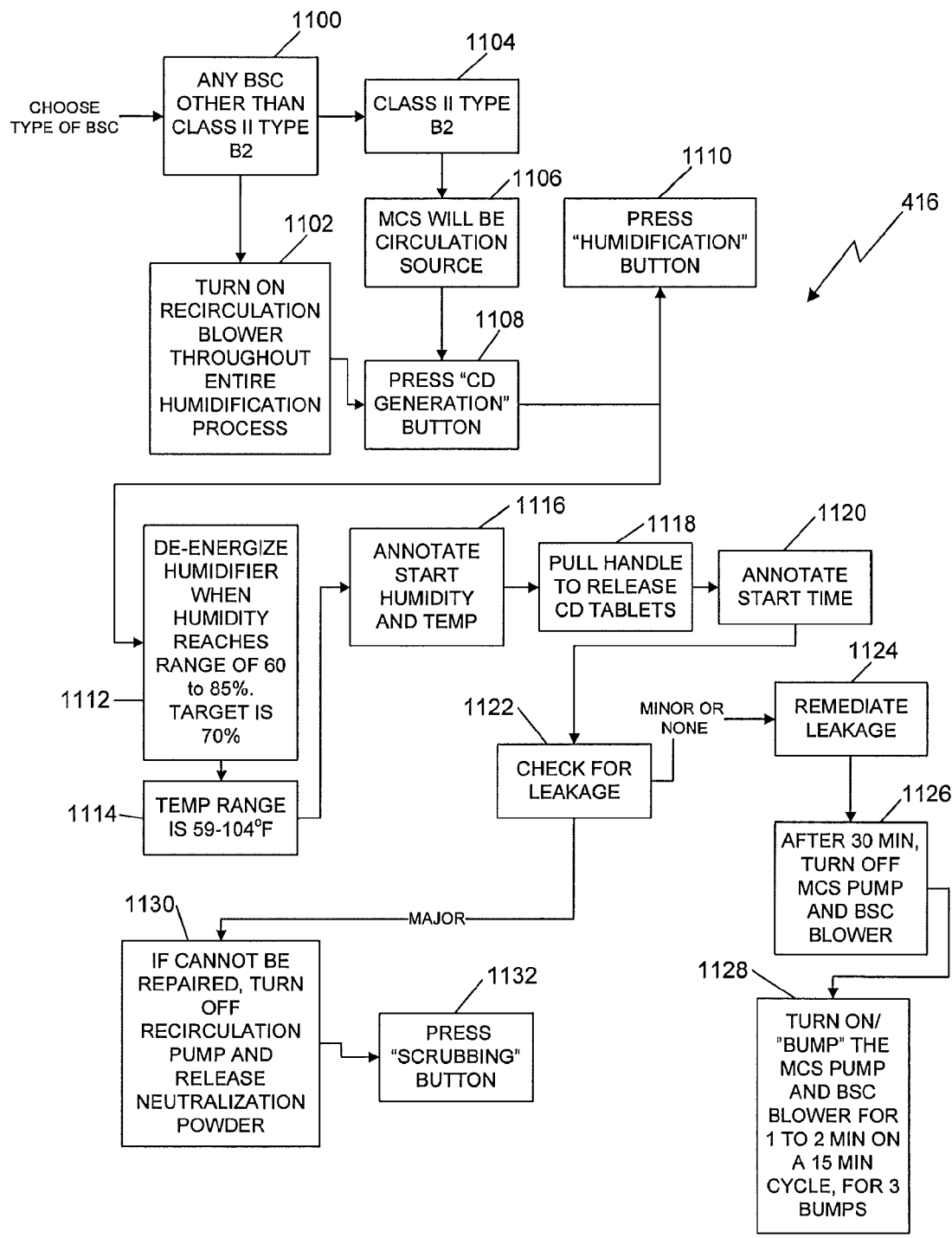
FIG. 11 is a flow chart of the decontamination cycle of FIG. 4

FIG. 11 shows the decontamination Cycle. Before beginning the cycle, the user verifies that a negative pressure secondary containment system is incorporated within the decontamination area—or that the BSC is located within an un-recirculated space with a pressure negative relative to all bordering areas, labs and hallways, etc.

At step 1100, step 1102 is performed for all type BSC's, with the exception of the Class II type B2.

At step 1102, the user turns on the recirculation blower throughout the entire humidification process to distribute the water vapor.

At step 1104, for the Class II type B2 step 1106 is performed.

At step 1106, the MCS will be the circulation source for the entire decontamination process.

At step 1108, the user activates the switch on the control box for, "CD Generation", in order to energize the recirculation pump.

At step 1110, the user activates a "Humidification" control in order to activate the hand held humidifier within the BSC. The MCS pump is still operating.

At step 1112, the user de-energizes the hand held humidifier when the internal humidity is in a range of 60 to 85%, with a target value of 70%.

At step 1114, the user checks whether the temperature is in the permissible temperature range. E.g., 59-104° F. (15-40° C.), typically above 80° F. (27° C.) after humidification process.

At step 1116, the user notes the start Temperature and Relative Humidity.

At step 1118, the user actuates (e.g., pulls the handle 220 for) the $ClO_2$ dispensing cylinder and the $ClO_2$ generating tablets drop into the bubbler reservoir. This constitutes the beginning of the decontamination cycle.

At step 1120, the user notes the decontamination starting time. An optional Active Chemical Sampling may commence at this point.

At step 1122, the user checks for leakage around the enclosure and MCS connections.

At step 1124, the user remediates any minor leakage if found.

At step 1126, if there is no significant leakage, let the BSC blower and the MCS pump operate. After 30 minutes from the introduction of the ClO2 tablets, turn off the MCS pump and BSC blower.

At step 1128, the user turns on, or "Bumps", the MCS pump and BSC blower(s) for 1 to 2 minutes on a 15 minute cycle to distribute the ClO2 gas through dead legs and exhaust filters. There may be a total of (3) bump cycles.

At step 1130, if major leakage is found and cannot be immediately repaired and deemed a failure, cease the decontamination cycle. Turn off the recirculation pump and, release the neutralization powder.

At step 1132, the user turns on the scrubbing blower. Also, before turning on the blower, the user leaves the area; waiting at least 15 minutes before starting the investigation of the cause.

Figure 12:
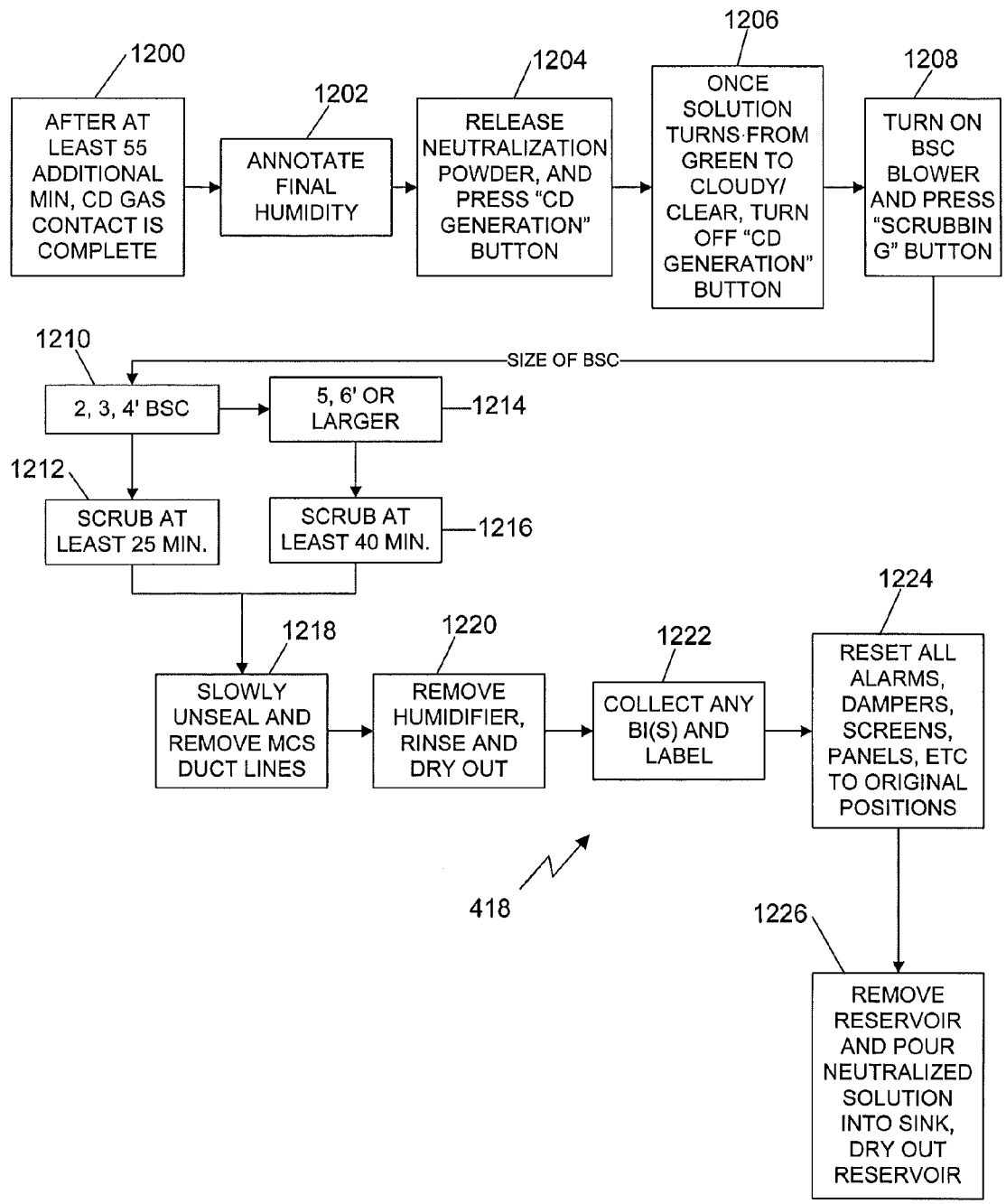
FIG. 12 is a flow chart of the scrubbing cycle of FIG. 4.

FIG. 12 is a flow chart of the Scrubbing Cycle

At step 1200, after at least an additional 55 minutes, or a total of 85 minutes after the introduction of the ClO2 generating tablets, the ClO2 gas contact cycle is complete.

At step 1202, the user notes the final Relative Humidity.

At step 1204, the user pulls the handle on the neutralizer dispensing cylinder to allow the neutralizing powder mixture to drop into the ClO2 solution reservoir. There should be some bubbling (primarily carbon dioxide).

At step 1206, once the powder drops into bowl, the user turns on the CD recirculation pump. This will agitate the water enough to mix the neutralizer into the water. Once the solution turns from green to a cloudy/clear color, the user shuts off the CD recirculation pump.

At step 1208, the user turns on the BSC's blower and the MCS blower (Button labeled "Scrubbing").

At step 1210, if the model is a 2, 3 or 4 ft model, step 1212 is performed.

At step 1212, the user allows the scrubbing cycle to continue at least 25 minutes for 2, 3, and 4 foot models.

At step 1214, if the model is a 5', 6' or larger BSC, step 1216 is performed.

At step 1216, the user allows the scrubbing cycle to continue at least 40 minutes for 5', 6' or larger BSC's. After 25 to 40 minutes one may begin to slowly unseal the enclosure. If there is still a significant chlorine type odor, the user reseals and lets scrubbing continue for another 10 minutes.

At step 1218, upon completion of the scrubbing cycle, all sealing materials and MCS duct lines may be removed from the BSC.

At step 1220, the user removes the hand held humidifier from the cabinet and drain residual water. There will be some residual $ClO_2$ dissolved within the liquid. Rinse out and dry for future use.

At step 1222, the user collects any biological indicators and label appropriately for later identification.

At step 1224, the user resets all, alarms, dampers, exhaust protective screens, and any panel removed to their original positions to seal the BSC.

At step 1226, the bubbler solution may be disposed after the scrubbing cycle has been completed. The user removes the reservoir, pour the resulting solution into a sink and rinse and dries out the reservoir.

Figure 13:
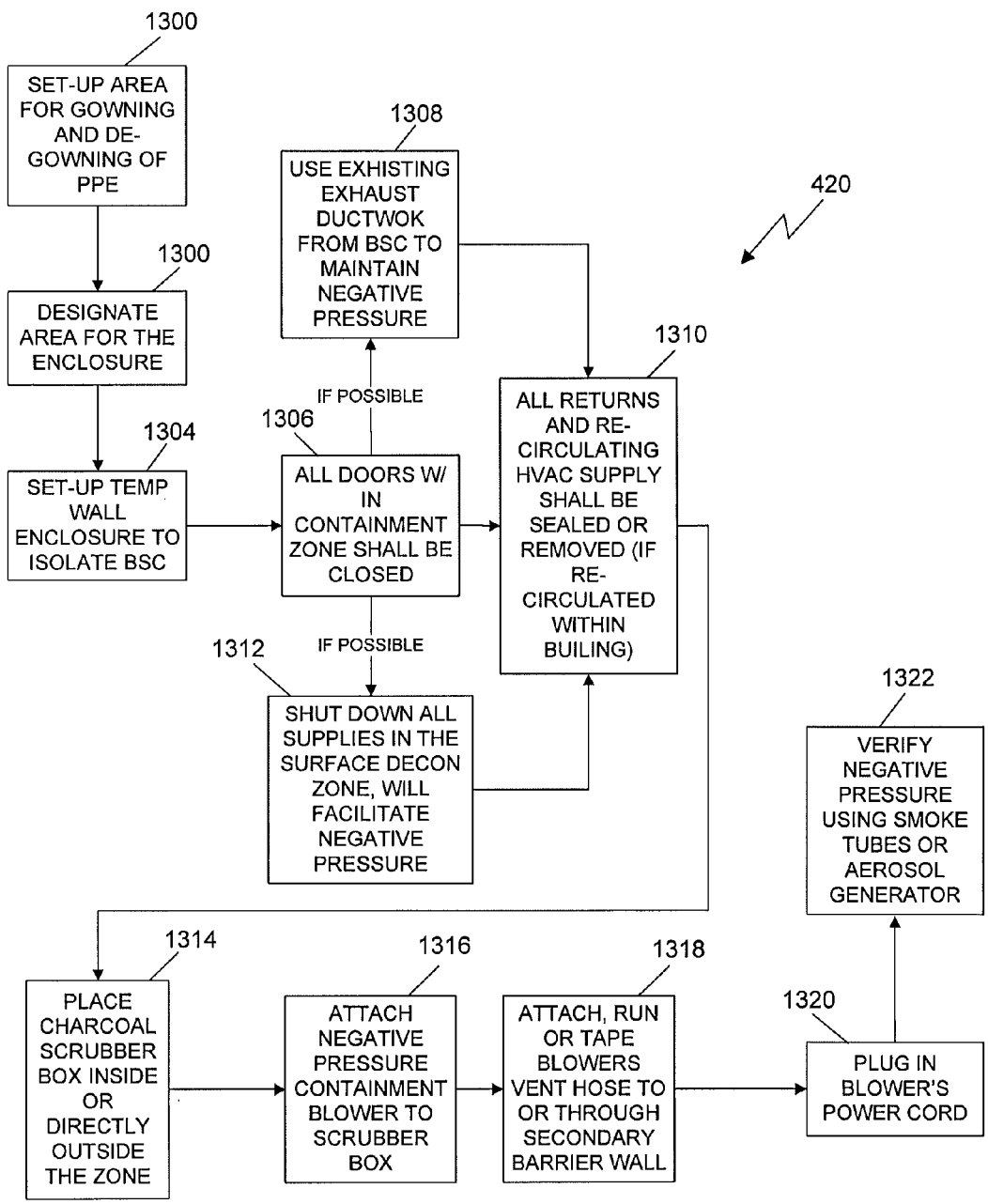
FIG. 13 is a flow chart of the secondary containment process of FIG. 4.

FIG. 13 shows an Optional Secondary Containment procedure.

At step 1300, the user sets-up or designates an area for gowning of Personal Protective Equipment (PPE), and sets-up or designates an area for de-gowning of PPE.

At step 1302, the user designates an area for the enclosure.

At step 1304, if existing physical walls are not available, the user set-up a temporary wall enclosure (which may be constructed with four 12' spring loaded poles, head, plate, tether and grip disks) and shroud with polyethylene film to isolate the BSC from the non-decontamination area (public area). The user overlaps sheets (e.g., polyethylene) on a wall to create a temporary entry into the zone.

At step 1310, openings, seams, seals, penetrations, pass-throughs may be taped up, sealed to prevent any potential escape of gasses and facilitate a negative pressure.

At step 1306, doors within the secondary containment zone are closed to maintain the constant negative pressure to the surrounding areas. The doors are not sealed since the make-up exhaust air volumes may draw from these areas and may provide egress from the area.

At step 1312, if possible, the user shuts down all supplies in the surface decontamination zone. No additional supply air should be tied into temporary wall enclosure. This will facilitate negative pressure within the zone to contain potential decontamination gases. The existing exhaust ductwork from the BSC may be used to maintain a negative pressure within this zone. No charcoal scrubbing is then required. All returns (if re-circulated within the building) are sealed or removed. All re-circulating HVAC supply (if re-circulated within the building) are sealed or removed.

At step 1314, dependent upon the available working floor space within the secondary containment zone, the user places the charcoal scrubber box inside or directly outside the zone along one wall.

At step 1316, the user attaches the negative pressure containment blower to the charcoal scrubber box.

At step 1318, the user attaches, runs and/or tapes the blowers vent hose to or through the secondary barrier wall.

At step 1320, the user plugs the blower's power cord into a nearby outlet to energize the blower. This will create the negative pressure within the barrier.

At step 1322, the user verifies that differential pressure from within the secondary containment system zone to surrounding ambient zone is negative. Airflow direction may be verified using ventilation smoke tubes or hand-held aerosol generator. This pressure should be monitored periodically throughout the entire process.

An optional set-up without a secondary containment barrier may be used if the following conditions are met:
a. The BSC is located in an un-recirculated negative pressure space.
b. All unassociated decontamination personnel and or laboratory animals are removed throughout the entire process.

Figure 14:
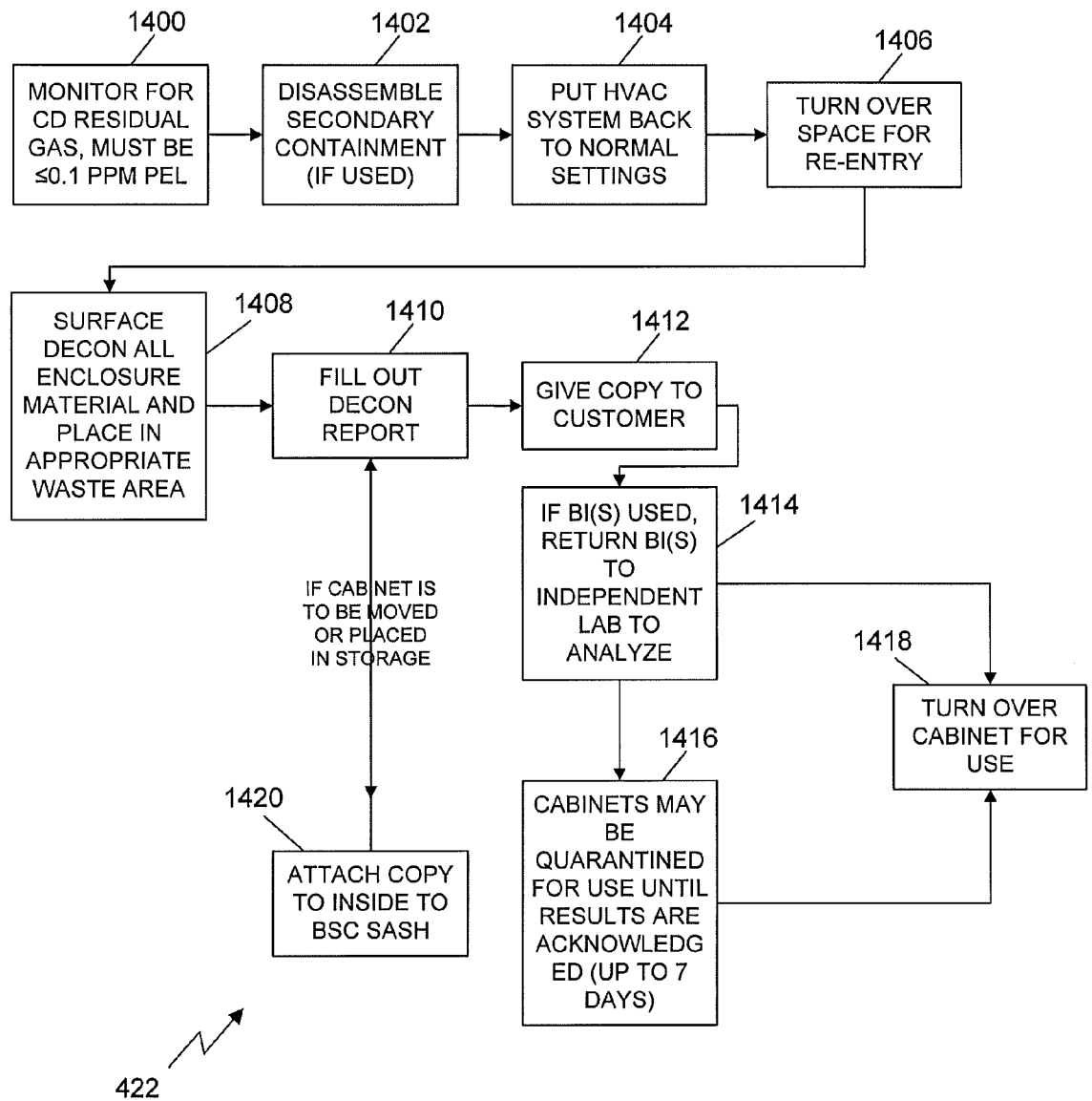
FIG. 14 is a flow chart of the post-decontamination procedure of FIG. 4.

FIG. 14 shows the final procedure performed when Decontamination is Complete.

At step 1400, the user monitors for $ClO_2$ residual gas within the immediate area after completing the clean up. Sampled levels must be below the acceptance levels before proceeding further. Chlorine Dioxide (Acceptance of $\leq 0.1$ ppm PEL). Release of the room for customer re-occupancy should be based on the lack of obnoxious odors related to the decontamination process.

At step 1402, the user disassembles the secondary containment system or zone.

At step 1404, the user returns the HVAC system's parameters that were changed back to normal settings.

At step 1406, the user turn over space for re-entry into the space to resume normal operations.

At step 1408, all enclosure materials, polyethylene film will be surface decontaminated, if applicable, and placed in the appropriate waste. The user will dispose of in accordance with the customer's site specification.

At step 1410, the final decontamination report will be filled out completely.

At step 1412, the report is printed or emailed at the completion of the job. (Typically the contractor following the decontamination needs the report verification immediately to continue work.)

At step 1414, the user returns Biological Indicators (BI) to an independent contract laboratory to monitor growth, thus determining the effectiveness of the decontamination (when requested).

At step 1416, cabinets may be quarantined for use until results from biological indicators are acknowledged.

At step 1418, the user turns over the cabinet for use after the agreed upon waiting period.

At step 1420, if the cabinet is to be moved or placed in storage, the user attaches a copy of the completed decontamination report to the inside of the sash.

Many variations and options are may be included in various embodiments.

In some embodiments, a gas tight sealing panel with a 360 degree rotating connector is provided for the return of the decontaminating gas. Gas tight sealing duct ports of various diameters may be used for the return of the decontaminating gas.

In some embodiments, gas tight sealing duct caps of various diameters are provided for the return of the decontaminating gas.

A gas tight return line may be provided to transfer gas for the device under decontamination and back to the MCS unit.

In some embodiments, the dispensing assembly has a clear gas tight threaded bubbler reservoir to be filled with appropriate quantity of tap water, the typical quantity of tap water is 1 liter.

In some embodiments, the dispensing assembly has a clear gas tight reservoir that has an internal ¼" (1.27 cm) tygon 360 degree directional tubing is hanging to the bottom of the reservoir to provide bubbling or sparging (sparging, also known as gas flushing, is the MCS technique which involves bubbling a chemically inert gas or ambient air through the liquid or tap water. This is used to remove dissolved gases (e.g. $ClO_2$) from the liquid) of the water to generate the gas from a solid ClO2 generation source. (do you need the exact chemistry at this time?)

In some embodiments, the dispensing assembly has a CD tablet dispensing cylinder with a gas tight removable cap.

In some embodiments, the dispensing assembly has a CD tablet dispensing cylinder with a slide dispensing damper connected to a exterior color coded control knob all gas tight design.

In some embodiments, the dispensing assembly has a neutralizer dispensing cylinder with a gas tight removable cap.

In some embodiments, the dispensing assembly has a neutralizer dispensing cylinder with a slide dispensing damper connected to an exterior color coded control knob, all gas tight design. The waste liquid from the MCS bubbler dispensing bowl remaining upon completion of the decontamination cycle is acidic (pH~2) and contains aqueous CD until the liquid neutralization has been completed with is the purpose of this design.

In some embodiments, the neutralization powder may be a proprietary mixture.

In some embodiments, the dispensing assembly provides means of introduction of chemicals in a controlled gas tight design without breaking of any seals.

In some embodiments, the charcoal scrubber box has an inlet incorporating a charcoal retention screen with a gas tight design.

In some embodiments, the charcoal scrubber box has an outlet incorporating a charcoal filtering HEPA filter with a gas tight design.

In some embodiments, the control box has combination power/breaker switches and LED illustration lighting.

Preferably, the piping design incorporates the two pumps or blowers, charcoal scrubber box, dispensing assembly, and provisions to attach the supply and return lines all incorporated into one system. One blower is for the generation of $ClO_2$ The second blower is for the scrubbing or removal of the $ClO_2$ gas.

The MCS 2345 allows one to provide complete decontamination services in less than 4 hours, including setup and tear down of Biological Safety Cabinets (BSC) or devices (e.g., Casework, Cabinets, HLF's or VLF's, Containment Devices, CFH's, Centrifuges, Refrigerators, Freezers, Washers, Water Baths, Shakers, Bio-reactors, Tanks, CIP's, Computers, or any other lab or productions equipment).

Other Items may be incorporated within the decontamination space, and can be placed within the BSC.

Examples of BSC's which the MCS is compatible with, are all classes and type classifications as with all other types of contaminate equipment or other potentially contaminated devices or spaces.

The MCS 2345 will provide recirculation of humidity and decontamination gases through the BSC or device with and without the aid of the devices' internal air circulation blower(s) if applicable. For the Class II type B2 the MCS will be the circulation source for the entire decontamination process.

The MCS 2345 will provide recirculation of humidity and decontamination gases through the BSC upstream and downstream exhaust HEPA filter plenum to eliminate the "dead leg" sealing portion with and without the aid of the device's internal air circulation blower.

Some embodiments include gas tight sealing panels for the introduction of the decontaminating gas. The sealing panels have a port to introduce a power cord to energize a humidity generator within the device or space under decontamination.

A gas tight sealing panel may be included for "tenting method" or temporary spaces to contain the gas for the introduction of the decontaminating gas. Similarly, A gas tight sealing duct port of various diameters may be included for the introduction or return of the decontaminating gas to a BSC (Type B2). A gas tight non-directional introduction line may be provided to transfer the gas into the device.

Although the invention has been described in terms of exemplary embodiments, it is not limited thereto. Rather, the appended claims should be construed broadly, to include other variants and embodiments of the invention, which may be made by those skilled in the art without departing from the scope and range of equivalents of the invention.

What is claimed is:

1. A system comprising:
a portable source of gaseous chlorine dioxide (CD), the portable source having a first source coupling and a first return coupling for sealingly connecting the portable source to a CD generation flow path comprising at least one gas conduit, the CD generation flow path comprising a second source coupling and a second return coupling for sealingly connecting the portable source to a device to be treated with the CD generation flow path, wherein the portable source includes:
a sealed reservoir for containing a volume of water,
a sealable first dispenser connected to the sealed reservoir for adding a solid CD precursor to the water, wherein the sealable first dispenser includes a solid or powder dispensing cylinder with a dispensing damper slidably mounted therein; and
a sparging tube for introducing air or an inert gas into the water in the sealed reservoir, for releasing the gaseous CD; and
a portable scrubber having a third coupling for sealingly connecting to a scrubbing flow path comprising at least one gas conduit for removing the CD from the device, the at least one gas conduit of the scrubbing flow path having a fourth coupling for connecting the device, to the scrubbing flow path.

2. The system of claim 1, further comprising:
a first blower in, the CD generation flow path for pumping the CD into the device, and
a second blower in the scrubbing flow path for pumping the CD through the portable scrubber.

3. The system of claim 1, wherein the first dispenser includes:
a solid or powder receptacle for feeding the solid CD precursor into an opening of the dispensing damper; and
a sealable, gas-tight cap for sealing the solid or powder receptacle.

4. The system of claim 1, wherein the second source coupling and second return coupling are configured for sealingly connecting the portable source to a temporary enclosed sealed space.

5. The system of claim 1, wherein the second source coupling and second return coupling are configured for sealingly connecting the portable source to a biological safety cabinet.

6. The system of claim 1, wherein the second source coupling and second return coupling are configured for sealingly connecting the portable source to a negative isolator.

7. The system of claim 1, wherein the second source coupling and second return coupling are configured for sealingly connecting the portable source to a positive isolator.

8. The system of claim 1, wherein the second source coupling and second return coupling are configured for sealingly connecting the portable source to an animal device.

9. The system of claim 1, wherein the second source coupling and second return coupling are configured for sealingly connecting the portable source to an incubator.

10. The system of claim 1, wherein the second source coupling and second return coupling are configured for sealingly connecting the portable source to a refrigerator.

11. The system of claim 1, wherein the second source coupling and second return coupling are configured for sealingly connecting the portable source to a freezer.

12. The system of claim 1, wherein the second source coupling and second return coupling are configured for sealingly connecting the portable source to a room.

13. A system comprising:
a portable source of gaseous chlorine dioxide (CD), the portable source having a first source coupling and a first return coupling for sealingly connecting to a CD generation flow path comprising at least one gas conduit, the CD generation flow path comprising a second source coupling and a second return coupling for sealingly connecting the portable source to a device to be treated with the CD generation flow path, wherein the portable source includes:
a sealed reservoir for containing a volume of water,
a sealable first dispenser connected to the sealed reservoir for adding a solid CD precursor to the water, and
a sparging tube for introducing air or an inert gas into the water in the sealed reservoir, for releasing the gaseous CD, a portable scrubber having a third coupling for sealingly connecting to a scrubbing flow path comprising at least one gas conduit for removing the gaseous CD from the device, the at least one gas conduit of the scrubbing flow path having a fourth coupling for connecting the device to the scrubbing flow path, wherein the portable scrubber includes a high efficiency particulate air (HEPA) filter using charcoal, through which the gaseous CD in the scrubbing flow path is to be pumped;

a first blower in the gaseous CD generation flow path for pumping the gaseous CD into the device, and a second blower in the scrubbing flow path for pumping the CD through the scrubber.

14. The system of claim 13, wherein the second blower is sized to provide a higher airflow volume than the first blower, for scrubbing the gaseous CD from the device to be treated.

15. The system of claim 13, further comprising a controller coupled to the first and second blowers, configured for selectably operating the first blower in a CD generation mode or operating the second blower in a scrubbing mode.

16. The system of claim 15, wherein:

the system further comprises a check valve between the second blower and the device to be treated, wherein said check valve is configured to permit one way flow from the second blower to the device to be treated, and prevent backflow from the device to be treated to the second blower.

17. A system comprising:

a portable source of gaseous chlorine dioxide (CD), the portable source having a first source coupling and a first return coupling for sealingly connecting to a CD generation flow path comprising at least one gas conduit, the CD generation flow path comprising a second source coupling and a second return coupling for sealingly connecting the portable source to a device to be treated with the CD generation flow path, wherein the portable source includes:

a sealed reservoir for containing a volume of water, a sealable first dispenser connected to the sealed reservoir for adding a solid CD precursor to the water, and a sparging tube for introducing air or an inert gas into the water in the sealed reservoir, for releasing the gaseous CD, a portable scrubber having a third coupling for sealingly connecting to a scrubbing flow path comprising at least one gas conduit for removing the gaseous CD from the device, the at least one gas, conduit of the scrubbing flow path having a fourth coupling for connecting the device to the scrubbing flow path, wherein the portable scrubber includes:

a charcoal container, and a foot valve screen coupled to the scrubbing flow path for dispersing the gaseous CD through the charcoal container;

a first blower in the gaseous CD generation flow path for pumping the gaseous CD into the device, and a second blower in the scrubbing flow path for pumping the gaseous CD through the scrubber.

18. A system comprising:

a portable source of gaseous chlorine dioxide (CD), the portable source having a first source coupling and a first return coupling for sealingly connecting to a CD generation flow path comprising at least one gas conduit, the CD generation flow path comprising a second source coupling and a second return coupling for sealingly connecting the portable source to a device to be treated with the CD generation flow path, wherein the portable source includes:

a sealed reservoir for containing a volume of water, a sealable first dispenser connected to the sealed reservoir for adding a solid CD precursor to the water, and a sparging tube for introducing air or an inert gas into the water in the sealed reservoir, for releasing the gaseous CD, a portable scrubber having a third coupling for sealingly connecting to a scrubbing flow path comprising at least one gas conduit for removing the gaseous CD from the device, the at least one gas conduit of the scrubbing flow path having a fourth coupling for connecting the device to the scrubbing flow path;

a first blower in the gaseous CD generation flow path for pumping the gaseous CD into the device, a second blower in the scrubbing flow path for pumping the gaseous CD through the scrubber; and a steam generator and a relative humidity meter, for humidifying the device prior to providing gaseous CD from the portable source of gaseous CD to the device.

19. A system comprising:

a portable source of gaseous chlorine dioxide (CD), the portable source having a first source coupling and a first return coupling for sealingly connecting to a CD generation flow path comprising at least one gas conduit, the CD generation flow path comprising a second source coupling and a second return coupling for sealingly connecting the portable source to a device to be treated with the CD generation flow path, wherein the portable source includes:

a sealed reservoir for containing a volume of water, a sealable first dispenser connected to the sealed reservoir for adding a solid CD precursor to the water, a sparging tube for introducing air or an inert gas into the water in the sealed reservoir, for releasing the gaseous CD, and a sealable second dispenser connected to the sealed reservoir for adding a neutralizing chemical to the water and solid CD precursor; and a portable scrubber having a third coupling for sealingly connecting to a scrubbing flow path comprising at least one gas conduit for removing the CD from the device, the at least one gas conduit of the scrubbing flow path having a fourth coupling for connecting the device to the scrubbing flow path.

20. A method of using the system of claim 13, wherein the at least one gas conduit includes source and return gas conduits, the method comprising:

connecting the source gas conduit and a return gas conduit to supply and return fittings of the device to be treated, and to the couplings of the portable source of gaseous chlorine dioxide (CD), so as to form the CD generation flow path connecting the portable source to the device;

pumping gaseous CD from the portable source through the device to be treated;

returning the gaseous CD from the device to be treated to the portable source;

connecting the portable source and return gas conduits to supply and return fittings of a portable scrubber to form a scrubbing flow path;

removing, the gaseous CD from the device by pumping gas from the device through the portable scrubber; and returning the scrubbed gas from the portable scrubber to the device to be treated.

21. The method of claim 20, further comprising:
adding a solid CD precursor to water in a sealed reservoir within the source; and
sparging the water to emit, the gaseous CD.

22. The method of claim 21, wherein the adding includes sliding a dispensing damper within a solid or powder dispensing cylinder to add the solid CD precursor.

23. The method of claim 22, wherein the adding includes:
feeding the CD precursor into a solid receptacle or powder receptacle adjacent the dispensing damper; and
sealing the solid receptacle or powder receptacle with a gas-tight cap.

24. The method of claim 20, further comprising adding a neutralizing chemical to the water and gaseous CD precursor after the device is treated with the gaseous CD.

25. The method of claim 20, wherein said pumping gas from the device through the scrubber includes forcing the gas in the scrubbing flow path through a bed of charcoal.

26. The method of claim 20, wherein said pumping gas from the device through the scrubber includes forcing the gas in the scrubbing flow path through a high efficiency particulate air (HEPA) filter.

27. The method of claim 20, wherein:
a first blower in the CD generation flow path is used for pumping the gaseous CD from the portable source into a tent surrounding the device to be treated, and
a second blower in the scrubbing flow path is used for pumping gas from the tent through the portable scrubber.

* * * * *

UNITED STATES PATENT AND TRADEMARK OFFICE
CERTIFICATE OF CORRECTION

PATENT NO. : 8,524,167 B2  
APPLICATION NO. : 12/759929  
DATED : September 3, 2013  
INVENTOR(S) : Michael A. Regits et al.

Page 1 of 1

It is certified that error appears in the above-identified patent and that said Letters Patent is hereby corrected as shown below:

In the Claims:

Claim 1, Column 16, Line 10 – delete "device," and insert -- device --.

Claim 2, Column 16, Line 13 – delete "in," and insert -- in --.

Claim 20, Column 18, Line 64 – delete "removing," and insert -- removing --.

Claim 21, Column 19, Line 4 – delete "emit," and insert -- emit --.

Signed and Sealed this  
Twenty-third Day of June, 2015

Michelle K. Lee  
*Director of the United States Patent and Trademark Office*